US006841537B1

(12) United States Patent
Joshi et al.

(10) Patent No.: US 6,841,537 B1
(45) Date of Patent: Jan. 11, 2005

(54) COMBINATION THERAPY USING NUCLEIC ACIDS AND CONVENTIONAL DRUGS

(75) Inventors: Phalgun B. Joshi, Vancouver (CA); Ian C. Mortimer, North Vancouver (CA); Patrick M. S. Tam, Vancouver (CA); Ian MacLachlan, Vancouver (CA); Roger W. Graham, Vancouver (CA)

(73) Assignee: Protiva Biotherapeutics Inc., Burnaby (CA)

( * ) Notice: Subject to any disclaimer, the term of this patent is extended or adjusted under 35 U.S.C. 154(b) by 0 days.

(21) Appl. No.: 09/295,663

(22) Filed: Apr. 21, 1999

Related U.S. Application Data

(60) Provisional application No. 60/082,665, filed on Apr. 22, 1998, provisional application No. 60/111,635, filed on Dec. 9, 1998, and provisional application No. 60/111,637, filed on Dec. 9, 1998.

(51) Int. Cl.[7] .................... A01N 61/00; A61K 31/70; C07H 21/02
(52) U.S. Cl. ..................... 514/44; 536/23.1; 514/1
(58) Field of Search .................... 514/44, 2; 435/172.3, 435/240.1, 240.2, 240.21, 320.1

(56) References Cited

U.S. PATENT DOCUMENTS

| 4,405,712 | A |   | 9/1983  | Vande Woude et al.       |
|-----------|---|---|---------|--------------------------|
| 5,571,797 | A |   | 11/1996 | Ohno et al.              |
| 5,580,859 | A |   | 12/1996 | Felgner et al. ... 514/44 |
| 5,589,466 | A |   | 12/1996 | Felgner et al. ... 514/44 |
| 5,591,601 | A |   | 1/1997  | Wagner et al. ... 435/69.1 |
| 5,676,954 | A |   | 10/1997 | Brigham ... 424/451      |
| 5,688,773 | A |   | 11/1997 | Chiocca et al. ... 514/44 |
| 5,705,385 | A | * | 1/1998  | Bally et al. ... 435/320.1 |
| 5,747,469 | A | * | 5/1998  | Roth et al. ... 514/44   |
| 6,041,252 | A | * | 3/2000  | Walker et al. ... 604/20 |

FOREIGN PATENT DOCUMENTS

| EP | 0 760 675 B1 | 1/2001  |
|----|--------------|---------|
| GB | 1548621      | 7/1979  |
| WO | WO 92/07943  | 5/1992  |
| WO | WO 94/00095  | 1/1994  |
| WO | WO 95/08994  | 4/1995  |
| WO | WO 96/40964  | 12/1996 |
| WO | WO 96/41875  | 12/1996 |

OTHER PUBLICATIONS

Bischoff et al., "An adenovirus mutant that replicates selectively in p53–deficient human tumor cells." Science, vol. 274: 373–376, Oct. 1996.*
Lee et al., "Taxol–dependent transcriptional activation of IL–8 expression in a subset of human ovarian cancer." Cancer Res. vol. 56: 1303–1308, Mar. 1996.*
Krek et al., "Cell synchronization." Methods Enzymol., vol. 254: 114–24, 1995.*
Crystal R., "Transfer of genes to humans: Early lessons and obstacles to success." Science, vol. 270: 404–410, 1995.*
Dachs et al., "Targeting gene therapy to cancer: A Review." Oncology Res., vol. 9: 313–325, 1997.*
Verma et al., "Gene therapy–promises, problems and prospects." Nature, vol. 389: 239–242, Sep. 1997.*
Deonarain M., "Ligand–targeted receptor–mediated vectors for gene delivery." Exp. Opin. Ther. Patents, vol. 8(1): 53–69, 1998.*
Miller et al., "Targeted vectors for gene therapy." FASEB, vol. 9:190–199, Feb. 1995.*
Orkin et al., "Report and recommendations of the panel to assess the NIH investment in research on gene therapy." pp. 1–20, Dec. 1995.*
Brigham, et al., *Am. J. Med. Sci.*, 298(4):278–281 (1989).
Cohen, *Immunol. Today*, 14(3):126–130 (1993).
Gavrieli, et al., *J. Cell Biol*, 119(3): 493–501 (1992).
Hyde, et al., *Nature*, 362:250–256 (1993).
Ikegami, et al., *Nature*, 275:458–460 (1978).
Keyomarsi, et al., *Cancer Research*, 51: 3602–3609 (1991).
Legendre, et al., *Pharm. Res.*, 9(10):1235–1242 (1992).
Lunardi–Iskandar, et al., *Clin. Exp. Immunol.*, 60:285–293 (1985).
Peters, *Nature*, 371:204–205 (1994).
Sherr, *Cell*, 73:1059–1065 (1993).
Son, et al., *Proc. Natl. Acad. Sci. USA*, 91: 12669–12672 (1994).
Tseng, et al., *Biotechnol. Bioeng.*, 50:548–554 (1996).
Wahl, et al., *Biochemistry*, 25:7821–7837 (1986).
White, et al., *J. Virol.*, 52(2):410–419 (1984).
Zabner, et al., *J. Biol. Chem.*, 270(32):18997–19007 (1995).
Zhu, et al., *Science*, 261:209–211 (1993).
Cone, et al., *Proc. Natl. Acad. Sci. USA*, 81:6349–6353 (1984).
Eglitis, et al., *Biotechniques*, 6(7):608–614 (1988).
Gilboa, et al., *BioTechniques*, 4(6):504–512 (1986).
Mann, et al., *Cell*, 33:153–159 (1983).
Miller, et al., *BioTechniques*, 7(9):981–990 (1989).

* cited by examiner

*Primary Examiner*—Deborah J. Reynolds
*Assistant Examiner*—Joe Woitach
(74) *Attorney, Agent, or Firm*—Townsend and Townsend and Crew LLP

(57) ABSTRACT

The present invention relates to methods for increasing the efficiency of transformation of cycling cells, the methods comprising synchronizing cells at a first stage of the cell cycle, and transforming the cells at a second stage of the cell cycle within about one cell cycle of the first stage with a genetically engineered nucleic acid that encodes a desired gene product. The invention further relates to cancer therapy and, in particular, to methods of efficiently transforming cancer cells with nucleic acids that encode gene products that inhibit the growth of cancer cells.

29 Claims, 17 Drawing Sheets

COMBINATION THERAPY USING NUCLEIC ACIDS AND CONVENTIONAL DRUGS

CROSS-REFERENCES TO RELATED APPLICATIONS

This application claims the benefit of U.S. Provisional Patent Application Ser. Nos. 60/082,665 filed Apr. 22, 1998 and 60/111,635, filed Dec. 9, 1998, which are incorporated herein by reference in their entirety for all purposes. This application is related to U.S. Provisional Patent Application Ser. No. 60/111,637, filed Dec. 9, 1998, which is incorporated herein by reference in its entirety for all purposes.

FIELD OF THE INVENTION

The present invention relates to methods of enhancing the therapeutic effect of a therapeutic nucleic acid by combining treatment with a conventional drug that is a cell cycle blocking agent. The present invention also pertains to methods for increasing the efficiency of transformation of cycling cells. The invention further relates to cancer therapy, and, in particular, to methods of efficiently transforming cancer cells with nucleic acids that encode gene products that inhibit the growth of cancer cells.

BACKGROUND OF THE INVENTION

The cell cycle consists of a cell division phase and the events that occur during the period between successive cell divisions, known as interphase. Most cell components are made continuously throughout interphase. As such; it is difficult to define distinct stages in the progression of the growing cell through interphase. One exception is DNA synthesis, since the DNA in the cell nucleus is replicated only during a limited portion of interphase. This period is denoted as the S phase (S=synthesis) of the cell cycle. The other distinct stage of the cell cycle is the cell division phase, which includes both nuclear division (mitosis) and the cytoplasmic division (cytokinesis) that follows. The entire cell division phase is denoted as the M phase (M=mitotic). The period between the M phase and the start of DNA synthesis, i.e., the S phase, is called the $G_1$ phase (G=gap). The period between the completion of DNA synthesis and the next M phase is called the $G_2$ phase. Nuclear membrane dissolution generally takes place immediately prior to cell division, during the M phase or the $G_2$/M interphase. Thus, interphase is composed of successive $G_1$, S, and $G_2$ phases. The duration of an entire cycle varies from cell type to cell type, but is often about 24 hours.

The cell contains exquisitely sensitive feedback control circuits that regulate entry into, exit out of and the events that occur during a given phase of the cell cycle. These circuits can, for example, prevent exit from the S phase if a fraction of a percent of DNA remains unreplicated, and they can block advance into anaphase in mitosis until all the chromosomes have aligned on the metaphase plate. The progression of a cell through the mitotic cycle is controlled by an array of regulatory factors that act as "checkpoints" and assure that the previous stage has been completed before the subsequent stage ensues. The relative abundance of these factors oscillates as the cell cycle advances, either by synthesis of a particular gene product or by chemical transformation, such as phosphorylation and dephosphorylation events. In particular, the progression of the cell to the next stage of its cycle is positively regulated by a family of master enzymes, i.e., cyclin-dependent kinases (see, Sherr, *Cell*, 73:1059–1065 (1993)). These enzymes are composed of two proteins, a regulatory subunit (the cyclin) and an associated catalytic subunit (the actual cyclin-dependent kinase or CDK), the levels of which vary with different phases of the cell cycle (see, Peters, G., *Nature*, 371:204–205 (1994)). Both cyclins and CDKs represent molecular families that encompass a variety of genetically related, but functionally distinct proteins.

Numerous protocols and reagents are used to synchronize cells in specific stages of the cell cycle. For example, cycling cells can be synchronized at a specific stage of the cell cycle by growth factor deprivation(see, Keyomarsi, et al., *Cancer Res*, 51:3602–3609 (1991). PCT Publication No. WO 94/00095 discloses the use of various calpain inhibitors to synchronize the cell cycle. Synchronization of cells, by itself, is a research tool that is not known to be useful for treating disease in a patient.

It is known, however, that compounds that induce cell cycle arrest (e.g., hydroxyurea, VM-26, cisplatin and taxol) can be used therapeutically for cancer treatment. The general theory behind this use is that cancer cells are among the most rapidly proliferating cells in multicellular organisms, and that they would therefore be more susceptible to compounds that disrupt or arrest cell cycling. Moreover, it is a developing medical practice to employ combinations of conventional drugs, including cell cycle blocking agents, for the treatment of cancer. Various combinations of conventional drugs known in the art are as follows: for acute lymphocytic leukemia—vincristine, prednisone, doxorubicin and L-asparaginase; for Hodgkin's disease—mechoroethamine, vincristine, procarbazine and prednisone (MOPP); for histiocytic lymphoma—cyclophosphamide, vincristine, procarbazine and prednisone (C-MOPP); and for testicular carcinoma—bleomycin, vinblastine, and cisplatin.

Although combinations of conventional drugs are being used to treat diseases, no combinations employ a combination of conventional drugs together with the newly developed gene drugs, i.e., expressible nucleic acids, therapeutic genes, etc.

Gene drugs have become available in recent years for the treatment of various types of diseases. A fundamental hurdle for gene drugs is delivery of the gene to the target or treatment site because large nucleic acids are rapidly degraded upon exposure to serum. However, this hurdle has been overcome for local and regional (i.e., inhalation or direct injection) delivery by the use of viral vectors, lipid complexes and the like. For systemic (i.e., intravenous) delivery, the hurdle has been overcome by the use of stable plasmid-lipid particles ("SPLPs") disclosed in PCT Publication No. WO 9640964, which is assigned to the assignee of the instant invention and which is incorporated herein by reference. SPLPs are fully encapsulated lipid-plasmid particles that are resistant to nuclease degradation, have low immunogenicity, and are of small size (<150 nm), thereby making them particularly well suited for long circulation lifetimes. Therapeutic uses for these SPLPs have been disclosed in U.S. patent applications Ser. Nos. 60/063,473; 60/073,598; 60/082,665; 60/086,917, all of which are assigned to the assignee of the instant invention and are incorporated herein by reference.

Son and Huang, *Proc. Natl. Acad. Sci.*, 91:12669–12672 (1994), reported that improved expression of a plasmid delivered directly to tumor cells can be obtained in tumor cells seven days after treatment with cisplatin. Other drugs, including vincristine, were not found to be effective. Son and Huang did not teach, suggest or appreciate the benefits associated with the synchronization of cells at the treatment site for enhanced use of therapeutic gene drugs. Further, Son and Huang neither taught not appreciated that the synchronization of cells could be used to increase the efficiency of transformation, nor did they teach or suggest that synchronized cells at certain stages of the cell cycle are more efficiently transformed with therapeutic genes.

SUMMARY OF THE INVENTION

The present invention provides methods of increasing the efficiency of cellular transformation of cycling cells, the methods comprising synchronizing cycling cells at a first stage of the cell cycle, and transforming these cells at a second stage within about an additional cell cycle with a genetically engineered nucleic acid that encodes a desired gene product. In another embodiment, the invention provides methods for killing a cycling cell, the methods comprising contacting a target population of cells with a first agent that synchronizes (for example, by transiently blocking progression of the cell cycle) the cells, and thereafter contacting the cell with a nucleic acid that transforms the cell within about an additional cell cycle. In a preferred embodiment, the first agent blocks the progression of the $G_1$, S, $G_2$, or mitosis stage of the cell cycle. The nucleic acid is preferably part of a lipid-nucleic acid particle (lipoplex) and encodes a desired gene product. The duration of contact with the first agent is advantageously limited to a first time period sufficient to block the progression of the cell cycle at a particular stage of the cell cycle or to synchronize cells at a particular stage of the cell cycle. The duration of contact with the nucleic acid is advantageously limited to a second time period whose timing and duration are sufficient for cells to be transformed.

Using the methods of the present invention, improved transfection of cells at the site of neoplasm by therapeutic genes is achieved after a period of cell cycle blocking, particularly at the $G_2$/M interphase or the M phase. For instance, when cells arrested in the $G_1$ phase with the cell blocker aphidicolin were allowed to synchronously proceed through the cell cycle and were transfected with a luciferase gene at specific points in the cell cycle, maximal luciferase transgene expression was found to coincide with the transition of cells from $G_2$/M phase into the $G_1$ phase of the subsequent cell cycle. Generally, cells are most amenable to transfection when the cells are incubated with lipoplexes during or just before mitosis. Plasmids may be more successfully delivered to the nucleus (the site of transcription) during this period, perhaps because of the limited amount of time plasmids are exposed to intra-cellular nucleases and other degradation elements before they are localized in the nucleus and transcribed. Alternatively, though less likely, the cells may be taking up, such as by endocytosis, more of the delivered plasmid during the period of cell cycle blockage, thus resulting in a proportionately higher expression.

Typically, it has been found that in a tumor containing unsynchronized cell populations, transfection preferably occurs in cells in the $G_2$/M phase. Such cells may represent less than 10% of the population at any given time. The remaining 90% either resist uptake of plasmid, or degrade or inhibit the plasmid before it is expressed in the nucleus. However, by employing the methods of the present invention, a greater population of cells are synchronized in a transfection/expression competent state at the time of exposure to the plasmid thereby resulting in improved expression of the gene at the tumor site.

The methods of the present invention are not limited to the transfection of malignant cells at the site of neoplasm, but can also include benign cells at the site of neoplasm. A wide variety of malignant and benign cells are present at most sites of neoplasm. The benign cells include macrophages and immune system cells, as well as normal healthy vascular endothelial cells which are induced by tumorigenic ones.

The choice of therapeutic gene may be selected according to the cell that is actually transfected. For example, if the vascular endothelium is targeted, then a therapeutic gene such as the gene encoding endostatin or angiostatin will successfully inhibit tumor growth.

The present invention is particularly useful when the anti-neoplastic drug is combined with the delivery of the herpes simplex virus thymidine kinase gene (HSV-TK), followed by treatment with the pro-drug ganciclovir. HSV-TK converts the pro-drug into a toxic analog (described in detail in U.S. patent application Ser. No. 60/073,598, the teachings of which are incorporated herein by reference). Transfection with HSV-TK results in a "bystander effect," wherein either the TK gene product or the toxic analog diffuses into neighboring cells where the toxic effect is also exerted. This system allows for greater cell killing from a limited number of transfection sites.

The present invention also encompasses improved methods for transfection of cells at organs or disease sites which are not cancerous. Using these methods, alternative therapeutic genes may be employed at these sites. For example, improved transfection of spleen cells using a gene encoding an immune stimulating peptide, such as IL-12, is taught herein.

The methods of the invention have self-evident utility as methods of improving tumor response to gene therapy and, more broadly, as methods of treating cancer in a patient

BRIEF DESCRIPTION OF THE DRAWINGS

FIG. 8(A) illustrates the pINEX L018 plasmid construct description and map, whereas

DETAILED DESCRIPTION OF THE INVENTION AND PREFERRED EMBODIMENTS

A. Introduction

Figure 1:
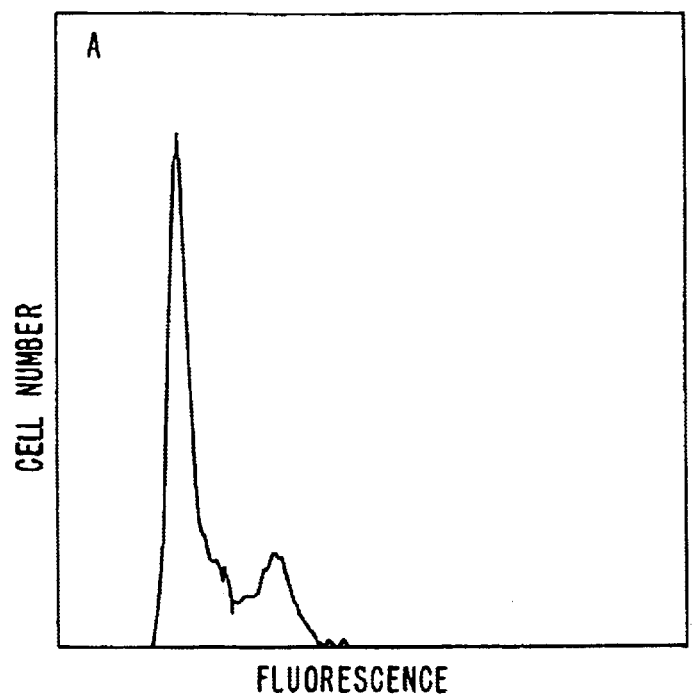
FIG. 1: Flow cytometric analysis of SK-OV-3 cells. Cells were treated for DNA content analysis as described in the Example Section. Shown are histograms of relative propidium iodide fluorescence versus number of cells. (A) An asynchronous culture containing proliferating cells gives a characteristic trimodal profile. The peak on the left corresponds to cells in the $G_1$ phase of the cell cycle with 2N amount of DNA; the peak to the right corresponds to cells in the $G_2$ phase with 4N DNA. The shoulder between the two peaks corresponds to the S phase in which the heterogeneous cells have a variable DNA content between 2N and 4N. (B) The aphidicolin treated cultures were effectively synchronized with greater than 95% of the cells arrested in the $G_1$ stage of the cell cycle.
Figure 1:
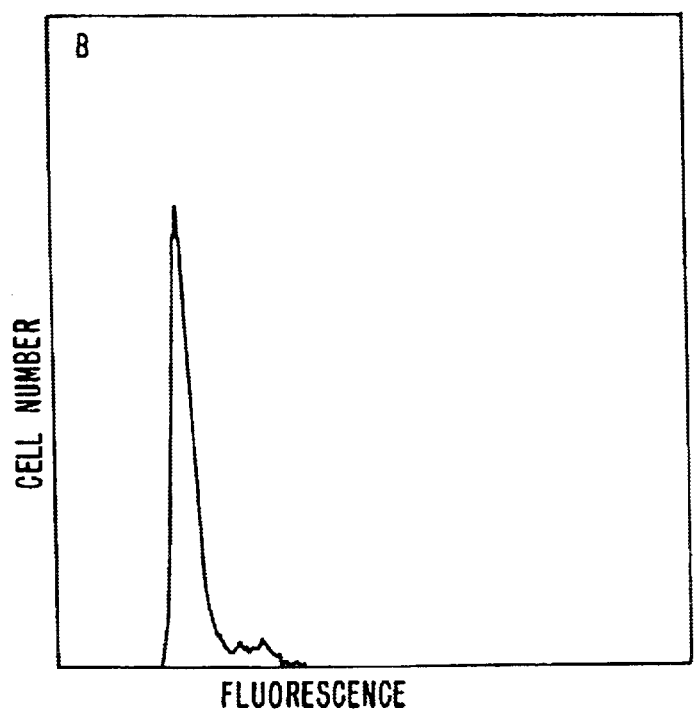

The present invention relates to methods for enhancing the therapeutic effects of a therapeutic nucleic acid by combining treatment with a conventional drug, X-rays or other form of radiation, all of which are cell cycle blocking agents.

The invention takes advantage of the surprising discovery that more efficient transformation of cells by therapeutic nucleic acids delivered to the cells (i.e., in a plasmid construct) can be achieved by minimizing the time between transfection of the plasmid and expression of plasmid in the nucleus. The methods of the invention are achieved by delivering the plasmid to cells that are synchronized at a stage in the cell cycle when the nuclear membrane is substantially dissolved, generally just prior to cell division. The cells at the disease or target site of interest can be synchronized by pretreatment with a drug or with some form of radiation (such as X-ray) that is a cell cycle blocking agent. As further described hereinbelow, and without intending to be bound by any theory, it is proposed that therapeutic nucleic acids which are delivered according to the invention are rapidly expressed in the cell nucleus and spend a reduced amount of time exposed to intracellular nucleases and other degradative metabolic processes; thereby resulting in a more efficient transformation of these cycling cells and an enhanced therapeutic effect of the therapeutic nucleic acid.

Definitions

Unless defined otherwise, all technical and scientific terms used herein have the same meaning as commonly understood by one of ordinary skill in the art to which this invention belongs. All literature and patent references cited herein are hereby incorporated by reference for all purposes.

The following abbreviations are used herein: DC-Chol, 3β-(N-(N',N'-dimethylaminoethane)carbamoyl)cholesterol (see, Gaoet, et al., *Biochem. Biophys. Res. Comm.*, 179:280–285 (1991)); DDAB, N,N-distearyl-N,N-dimethylammonium bromide; DMRIE, N-(1,2-dimyristyloxyprop-3-yl)-N,N-dimethyl-N-hydroxyethyl ammonium bromide; DODAC, N,N-dioleyl-N,N-dimethylammonium chloride (see, commonly owned U.S. patent application Ser. No. 08/316,399, the teachings of which are incorporated herein by reference); DOGS, diheptadecylamidoglycyl spermidine; DOPE, 1,2-sn-dioleoylphoshatidyethanolamine; DOSPA, N-(1-(2,3-dioleyloxy)propyl)-N-(2-(sperminecarboxamido)ethyl)-N,N-dimethylammonium trifluoroacetate; DOTAP, N-(1-(2,3-dioleoyloxy)propyl)-N,N,N-trimethylammonium chloride; DOTMA, N-(1-(2,3-dioleyloxy)propyl)-N,N,N-trimethylammonium chloride; EPC, egg phosphatidylcholine; RT, room temperature; HEPES, 4-(2-hydroxyethyl)-1-piperazineethanesulfonic acid; HBS, HEPES buffered saline (150 mM NaCl and 20 mM HEPES); PEG-Cer-$C_{20}$, 1-O-(2'-(ω-methoxypolyethyleneglycol)succinoyl)-2-N-arachidoyl-sphingosine; PEG-Cer-$C_{14}$, 1-O-(2'-(ω-methoxypolyethyleneglycol)succinoyl)-2-N-myristoyl-sphingosine; PBS, phosphate-buffered saline; EGTA, ethylenebis(oxyethylenenitrilo)-tetraacetic acid; OGP, n-octyl β-D-glycopyranoside (Sigma Chemical Co., St. Louis, Mo.); POPC, palmitoyl oleoyl phosphatidylcholine (Northern Lipids, Vancouver, BC); QELS, quasielastic light scattering; TBE, 89 mM Tris-borate with 2 mM EDTA; and EDTA, Ethylenediaminetetraacetic acid (Fisher Scientific, Fair Lawn, N.J.).

The term "acyl" refers to a radical produced from an organic acid by removal of the hydroxyl group. Examples of acyl radicals include, but are not limited to, acetyl, pentanoyl, palmitoyl, stearoyl, myristoyl, caproyl and oleoyl.

The term "lipid" refers to any fatty acid derivative that is capable of forming a bilayer such that a hydrophobic portion of the lipid material orients toward the bilayer while a hydrophilic portion orients toward the aqueous phase. Hydrophilic characteristics can be derived from the presence of phosphato, carboxylic, sulfato, amino, sulfhydryl, nitro, and other like groups. Hydrophobicity can be conferred by the inclusion of groups that include, but are not limited to, long chain saturated and unsaturated aliphatic hydrocarbon getups and such groups substituted by one or more aromatic, cycloaliphatic or heterocyclic group(s). Preferred lipids are phosphoglycerides and sphingolipids, representative examples of which include phosphatidylcholine, phosphatidylethanolamine, phosphatidyiserine, phosphatidylinositol, phosphatidic acid, palmitoyloleoyl phosphatidylcholine, lysophosphatidylcholine, lysophosphatidylethanolamine, dipalmitoylphosphatidylcholine, dioleoylphosphatidylcholine, distearoylphosphatidylcholine or dilinoleoylphosphatidylcholine could be used. Other compounds lacking in phosphorus, such as sphingolipid and glycosphingolipid families are also within the group designated as lipid. Additionally, the amphipathic lipids described above may be mixed with other lipids including triglycerides and sterols.

The term "non-cationic lipid" refers to any of a number of lipid species which exist either in an uncharged form, a neutral zwitterionic form or an anionic form at physiological pH. Such lipids include, for example, diacylphosphatidylcholine, diacylphosphatidylethanolamine, ceramide, sphingomyelin, cephalin, cardiolipin and cerebrosides.

The term "cationic lipid" refers to any of a number of lipid species that carry a net positive charge at physiological pH. Such lipids include, but are not limited to, DODAC, DOTMA, DDAB, DOTAP, DC-Chol and DMRIE. Additionally, a number of commercial preparations of cationic lipids are available which can be used in the present invention. These include, for example, LIPOFECTIN® (commercially available cationic liposomes comprising DOTMA and DOPE, from GIBCO/BRL, Grand Island, N.Y., USA); LIPOFECTAMINE® (commercially available cationic liposomes comprising DOSPA and DOPE, from GIBCO/BRL); and TRANSFECTAM® (commercially available cationic liposomes comprising DOGS from Promega Corp., Madison, Wis., USA).

The term "cellular transformation" or, interchangeably, "transfection," as used herein, refers to the introduction of polyanionic materials, particularly nucleic acids, into cells. The term "lipofection" refers to the introduction of such materials using liposome or lipid-based complexes. The polyanionic materials can be in the form of DNA or RNA that is linked to expression vectors to facilitate gene expression after entry into the cell. Thus, the polyanionic material used in the present invention is meant to include DNA having coding sequences for structural proteins, receptors and hormones, as well as transcriptional and translational regulatory elements (i.e., promoters, enhancers, terminators and signal sequences) and vectors. Methods of incorporating particular nucleic acids into expression vectors are well known to those of skill in the art, but are described in detail in, for example, Sambrook, et al., MOLECULAR CLONING: A LABORATORY MANUAL (2 nd ed.), Vols. 1–3, Cold Spring Harbor Laboratory, (1989) or CURRENT PROTOCOLS IN MOLECULAR BIOLOGY, F. Ausubel, et al., ed. Greene Publishing and Wiley-Interscience, New York (1987), both of which are incorporated herein by reference.

"Cloning vectors" or, interchangeably, "vectors," as used herein, refer to viruses, plasmids or other nucleic acid molecules that are able to replicate in a chosen host cell. Expression vectors may replicate autonomously, or they may replicate by being inserted into the genome of the host cell using methods well known in the an. Vectors that replicate autonomously will have an origin of replication or autonomous replicating sequence (ARS) that is functional in the chosen host cell(s). Often, it is desirable for a vector to be usable in more than one host cell, e.g., in *E. coli* for cloning and construction, and in a mammalian cell for expression. "Expression vectors" contain all of the control elements for expression of gene products encoded by the vectors.

Conditions for "increasing the efficiency of cellular transformation" refer to conditions under which a higher percentage of cells in a target cell population (for example, the cells of a tumor) are transformed relative to a control population of cells. Preferably, at least 50% more cells, more preferably at least 2 times more cells and, even more preferably, greater than 10 times more cells are transformed relative to the control cells.

"A stage of the cell cycle when the nuclear membrane is substantially degraded" is generally late $G_2$ to M phase, but may be earlier. This may be ascertained by microscopic examination. "Cycling cells" are cells that are not permanently arrested in any portion of the cell cycle.

"Synchronizing cells at a stage of the cell cycle" means that a population of cells that are at different stages of the cell cycle are induced to remain at, or proceed to, a particular phase of the cell cycle, such that at least 10%, preferably 30%, more preferably 60%, and most preferably more than 90% of the cells are all in the same stage of the cell cycle.

Synchronizing generally means increasing the fraction of cells that are at a certain stage of the cell cycle. In a preferred embodiment, compounds or conditions that synchronize cells do so by arresting cells in a particular stage of the cell cycle. A "cell cycle blocker" or, interchangeably, a "cell cycle blocking agent" is a synchronizing compound or a radiation treatment, such as X-rays, that inhibits a cell from proceeding into a subsequent cell cycle phase to which the cell would proceed in the absence of the compound. Preferably, cell cycle blockers arrest the cell cycle without adversely affecting cellular processes (such as endocytosis) related to transformation, such as the uptake of DNA and gene expression.

The term "nucleic acid" refers to deoxyribonucleotides or ribonucleotides and polymers thereof in either single- or double-stranded form. Unless specifically limited, the term encompasses nucleic acids containing known analogues of natural nucleotides which have similar binding invades as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer, et al., *Nucleic Acid Res.* 19:5081 (1991); Ohtsuka, et al. *J. Biol. Chem.* 260:2605–2608 (1985); and Cassol, et al., 1992; Rossolini, et al., *Mol. Cell. Probes* 8:91–98 (1994)). The term nucleic acid is used interchangeably with gene, cDNA and mRNA encoded by a gene. Unless otherwise indicated, a particular nucleic acid sequence includes the perfect complementary sequence thereof The nucleic acids used in the method of the present invention can be isolated from natural sources, obtained from such sources as ATCC or GenBank libraries or prepared by synthetic methods. Synthetic nucleic acids can be prepared by a variety of solution or solid phase methods. Generally, solid phase synthesis is preferred. Detailed descriptions of the procedures for solid phase synthesis of nucleic acids by phosphite-triester, phosphotriester, and H-phosphonate chemistries are widely available. See, for example, Itakura, U.S. Pat. No. 4,401,796; Caruthers, et al., U.S. Pat Nos. 4,458,066 and 4,500,707; Beaucage, et al., *Tetrahedron Lett.*, 22:1859–1862 (1981); Matteucci, et al.,*J. Am. Chem. Soc.*, 103:3185–3191 (1981); Caruthers, et al., *Genetic Engineering*, 4:1–17 (1982); Jones, chapter 2, Atkinson, et al., chapter 3 and Sproat, et al., chapter 4 in *Oligonucleotide Synthesis: A Practical Approach*, Gait (ed.), IRL Press, Washington D.C. (1984); Froehler, et al., *Tetrahedron Lett.*, 27:469–472 (1986); Froehler, et al., *Nucleic Acids Res.*, 14:5399–5407 (1986); Sinha, et al. *Tetrahedron Lett.*, 24:5843–5846 (1983); and Sinha, et al., *Nucl. Acids Res.*, 12:4539–4557 (1984), all of which are incorporated herein by reference.

"Nucleic acid probes" or "primers" can be DNA or RNA fragments. DNA fragments can be prepared, for example, by digesting plasmid DNA, or by use of PCR, or synthesized by either the phosphoramidite method described by Beaucage and Carruthers, *Tetrahedron Lett.*, 22:1859–1862 (1981), or by the triester method according to Matteucci, et al., *J. Am. Chem. Soc.*, 103:3185 (1981), both of which are incorporated herein by reference. A double stranded fragment may then be obtained, if desired, by annealing the chemically synthesized single strands together under appropriate conditions or by synthesizing the complementary strand using DNA polymerase with an appropriate primer sequence. Where a specific sequence for a nucleic acid probe is given, it is understood that the complementary strand is also identified and included. The complementary strand will work equally well in situations where the target is a double-stranded nucleic acid.

The phrase "a nucleic acid sequence encoding" refers to a nucleic acid that contains sequence information for a structural RNA, such as a rRNA, a tRNA, or the primary amino acid sequence of a specific protein or peptide, or a binding site for a transacting regulatory agent. This phrase specifically encompasses degenerate codons (i.e., different codons which encode a single amino acid) of the native sequence or sequences which may be introduced to conform with codon preference in a specific host cell.

The "gene product of the nucleic acid" refers to an mRNA, structural RNA such as rRNA, a tRNA, or a specific protein or peptide. This gene product may be directly or indirectly toxic. It may induce apoptosis or differentiation, or the transcript alone may incapacitate the target cell (i.e., a ribozyme or antisense product; or a protein with "nuclear jamming" ability).

The term "effective amount" means an amount or dosage of a given substance that is sufficient to produce a desired result The desired result can be a subjective or objective improvement, such as a clinical improvement, in the recipient of the dosage, a decrease in tumor size, a decrease in the rate of growth of cancer cells; or a decrease in metastasis.

"Toxic" means that a compound has a deleterious effect on target cells, such as cancer cells. A toxic compound kills, slows the growth and/or alters the metabolism of the target cell.

A "therapeutic gene" is one whose gene product performs a clinically useful function. For example, where the therapeutic gene is used to transform cancer cells, the therapeutic gene will inhibit the growth of the cancer cells. The therapeutic gene is preferably one whose gene product has low toxicity to non-target tissues, and high toxicity to the disease (e.g. cancer) site. For example, when delivered in the preferred lipid-nucleic acid (e.g., lipid-plasmid particles) particles of the invention, the gene product preferably has greater toxicity to tumor cells than liver or spleen cells, where a large portion of particles can normally be cleared. Alternatively, a therapeutic gene may be delivered to a treatment site, which is not a disease site, but which activates an immunologic or other response which is then favorable for the amelioration of the disease or disorder being treated. Examples of therapeutic genes useful in the methods of the present invention include; but are not limited to, genes for: pro-apoptotic proteins; tumor suppressors (e.g., p53, Rb1 (Retinoblastoma), etc.); cytokines (such as Interleukin-2, Interleukin-12, etc.); heat shock proteins; immunogenic antigens (such as tumor-specific proteins, etc.); genes activated in embryos only; Endostatin, Angiostatin, Thrombospondin, and other inhibitors of angiogenesis; Enzymes used in GDEPT combinations (i.e., suicide genes used in conjunction with a non-toxic pro-drug), such as Thymidine Kinase from Herpes simplex virus (HSV-TK); cytosine deaminase; porfirin; TIMP-2 (tissue inhibitor of metallo proteinase-2); plant, bacterial or fungal toxin genes, such as saporin, ricin, diphtheria toxin, cholera toxin; viral protein genes, such as E1A; mutated E6; SV40 Tag or viral protein genes which effect plasmid maintenance and/or copy number, such as EBNA-1; transcription plasmids encoding ribozymes or antisense oligonucleotides, Adenosine Deaminase; CFTR—Cystic Fibrosis; GM-CSF, IL-4, IL-2, IL-7, IL-10; Carcineombryonic Antigen; HLA-B7; TNF; T-Cell Receptor Antibody; CEA; Ig; IFN-g; MART-1; Chimeric Antibody/FCR; Prostate Specific Antigen; anti-erbB-2; Single Chain Antibody; BRCA-1; Alpha-1 Antitrypsin; p47 phax; Fanconi Anemia Complementation Group C; Glucocerbrosidase; Iduronato-2-Sulfatase; Purine Nulceaside Phosphorylase. Other therapeutic genes are continually being discovered and can be used in the methods of the present invention. Therapeutic genes are generally delivered as part of an expression construct, although other formats are possible.

A "therapeutic gene" is one whose gene product performs a clinically useful function. For example, where the therapeutic gene is used to transform cancer cells, the therapeutic gene will inhibit the growth of the cancer cells. The therapeutic gene is preferably one whose gene product has low toxicity to non-target tissues, and high toxicity to the disease (e.g. cancer) site. For example, when delivered in the preferred lipid-nucleic acid (e.g., lipid-plasmid particles) particles of the invention, the gene product preferably has greater toxicity to tumor cells than liver or spleen cells, where a large portion of particles can normally be cleared. Alternatively, a therapeutic gene may be delivered to a treatment site, which is not a disease site, but which activates an immunologic or other response which is then favorable for the amelioration of the disease or disorder being treated. Examples of therapeutic genes useful in the methods of the present invention include, but are not limited to, genes for pro-apoptotic proteins; tumor suppressors (e.g., p53, Rb1 (Retinoblastoma), etc.); cytokines (such as Interleukin-2, Interleukin-12, etc.); heat shock proteins; immunogenic antigens (such as tumor-specific proteins, etc.); genes activated in embryos only; Endostatin, Angiostatin, Thrombospondin, and other inhibitors of angiogenesis; Enzymes used in Gene Directed Enzyme Prodrug Therapy ("GDEPT") combinations (i.e., suicide genes used in conjunction with a non-toxic pro-drug), such as Thymidine Kinase from Herpes simplex virus (HSV-TK); cytosine deaminase; porfirin; TIMP-2 (tissue inhibitor of metallo proteinase-2); plant, bacterial or fungal toxin genes, such as saporin, ricin, diphtheria toxin, cholera toxin; viral protein genes, such as E1A; mutated E6; SV40 Tag or viral protein genes which effect plasmid maintenance and/or copy number, such as EBNA-1; transcription plasmids encoding ribozymes or antisense oligonucleotides, Adenosine Deaminase; CFTR—Cystic Fibrosis; GM-CSF, IL-4, IL-2, IL-7, IL-10; Carcineombryonic Antigen; HLA-B7; TNF; T-Cell Receptor Antibody, CEA; Ig; IFN-g; MART-1; Chimeric Antibody/TCR; Prostate Specific Antigen; anti-erbB-2; Single Chain Antibody; BRCA-1; Alpha-1 Antitrypsin; p47 phax; Fanconi Anemia Complementation Group C; Glucocerbrosidase; Iduronato-2-Sulfatase; Purine Nulceaside Phosphorylase. Other therapeutic genes are continually being discovered and can be used in the methods of the present invention. Therapeutic genes are generally delivered as part of an expression construct, although other formats are possible.

"Apoptosis" is a process of programmed cell death that is defined by a number of characteristic phenomena, summarized in Cohen, *Immunol. Today* 14:126–30 (1993). For example, in apoptotic cells, the cytoplasm condenses, and the endoplasmic reticulum dilates to form vesicles which fuse with the cell membrane, producing characteristic cellular morphology. Changes in the nuclei include nuclear condensation, the formation of dense crescent-shaped aggregates of chromatin, nucleolus fragmentation, and formation of vesicles at or on the nuclear membrane. A classic signature of apoptosis is the cleavage of nuclear DNA into nucleosomal subunits. During apoptosis, endonucleases present in the cell cut the DNA in the linker regions between nucleosomes to release DNA fragments in integer multiples of 180–190 base pairs. The pattern of cleavage is believed to result from the vulnerability of the linker DNA between the nucleosomes to endonucleases. On gels, this gives rise to the appearance of a ladder as nucleosomal units are sequentially cleaved from the DNA. Observation of a classic DNA ladder is indicative of apoptosis. For example, cells are lysed and the high molecular DNA is removed by centrifugation. The aqueous phase is treated with proteinase K to digest proteins. After a phenol/chloroform extraction, the DNA is precipitated with salt and ethanol. The pellet is dissolved in deionized water and treated with about 500 $\mu$g/mL RNase A. The DNA is run on a 2% agarose minigel. Observation for a classic DNA ladders is made. A gel photograph can be taken. Cell death is verified by the demonstration of DNA fragmentation as represented by the ladder configurations on the gel (see, Gavrieli, Y., et al., *J. Cell Biol.* 119:493 (1992)). There are also a variety of other assays available for apoptosis such as "TUNEL" assays (see, White, et al., *J. Virol.* 52:410 (1984)). Growth inhibition may be assessed using a number of commonly sued assays, such as the methylcellulose assay (see, e.g., Lunardi-Iskandar, et al., *Clin. Exp. Immunol.* 60:285–293 (1985)).

The term "tumor cell" or "cancer cell" or "neoplastic cell" denotes a cell that demonstrates inappropriate, unregulated proliferation. A cell line is said to be "malignant" if, when the cell line is injected into a host animal, the host animal develops tumors or cancers that are anaplastic, invasive and/or metastatic. A "human" tumor is comprised of cells that have human chromosomes. Such tumors include those in a human patient, and tumors resulting from the introduction of a human malignant cell line into a nonhuman host animal if cells from such tumors have human chromosomes.

The terms "treating cancer," "cancer therapy" and the like refer generally to a treatment that causes any improvement in a mammal having a cancer, wherein the improvement can be ascribed to treatment with a lipid-nucleic acid particle, nucleic acid or therapeutic gene of the present invention. The improvement can be either subjective or objective. For example, if the mammal is human, the patient may note improved vigor or vitality or decreased pain as subjective symptoms of improvement or response to therapy. Alternatively, the clinician may notice a decrease in tumor size or tumor burden based on physical examination, laboratory parameters, tumor markers or radiographic findings.

In general, the present invention is directed to the treatment of solid or diffuse and/or metastatic cancers which consist of cells transfectable with lipid-nucleic acid particles, and which have a low proportion of necrotic and/or quiescent (i.e. non-dividing) cells. Examples include, but are not limited to, ovarian, colon, and lung cancers, gliomas and melanomas.

The following is a partial list of tumor models used in embodiments of the invention (they may be transformed in vitro and in vivo):

1) LS180 Human colon adenocarcinoma
2) SK-OV-3 Human ovarian carcinoma
3) U87 Human gliobastoma
4) B16 bl/6 Mouse melanoma
5) Lewis Lung carcinoma
6) MCA 207 Fibrosarcoma.

The phrase "inhibiting cell growth" or "inhibiting tumor growth" generally means that the size, mass, or rate of increase in mass, size, number and/or the metabolism of treated cells and/or tumors is lower as a result of treatment than that of nontreated cells and/or tumors. The growth of a cell line or tumor is said to be "inhibited" by a treatment if, when assayed by means such as radioisotope incorporation into the cells, the treated cells increase in number at a rate that is less than the proliferation rate of untreated control cells, and preferably at a rate that is less than about 50% of the untreated cell proliferation rate. More preferably, the growth rate is inhibited by at least 80%. Most preferably, growth is reversed (i.e., the tumor gets smaller). If growth is assayed by a means such as plating in methylcellulose, the growth of a cell line is said to be "inhibited" if the treated cells give rise to less than the number of colonies that grow from a like number of untreated cells. Preferably, the number of colonies from treated cells is less than about 70% of the number from untreated cells. More preferably, the number of colonies is decreased by at least 50%. "Inhibition of cell growth" also encompasses zero growth and, most importantly, consequent death of the tumor cells and eradication of the tumor. When measured in vivo, "inhibition of tumor growth" encompasses fewer or smaller tumors (for example, smaller diameter) as compared to control animals or untreated patients.

Inhibition can be evaluated by any accepted method of measuring whether growth or size of the tumor and/or increase in the number of cancerous or tumor cells has been slowed, stopped or reversed. This includes direct observation and indirect evaluation such as subjective symptoms or objective signs. The clinician may notice a decrease in tumor size or tumor burden (number of tumors) based on physical examination, laboratory parameters, tumor markers or radiographic findings. Alternatively, if the mammal is human, the patient may note improved vigor or vitality or decreased pain as subjective symptoms of improvement or response to therapy. Some laboratory signs that the clinician may observe as an indication of response to therapy include normalization of tests such as white blood cell count, red blood cell count, platelet count, erythrocyte sedimentation rate, and various enzyme levels such as transaminases and hydrogenases. Additionally, the clinician may observe a decrease in a detectable tumor marker such as prostatic specific antigen (PSA) or chorio embryonic antigen (CEA). Alternatively, other tests can be used to evaluate objective improvement such as sonograms, computerized axial tomography scans, nuclear magnetic resonance scans and positron emission testing.

C. Combination Therapy Employing Cell Cycle Blockers and Therapeutic Genes

As noted previously, the present invention relates to the surprising discovery that expression of a therapeutic nucleic acid, such as an expressible nucleic acid or gene, is improved using combination treatment with a cell cycle blocker. Without intending to be bound by any theory, one explanation for this mechanism is based on the theory that a greater proportion of exogenous nucleic acids will be expressed if, after transfection, they are rapidly translocated to the cell nucleus, i.e., the site of transcription, thereby avoiding extended exposure to intracellular (cytosolic) nucleases, etc. Based on this theory, it is suggested that pretreatment with a cell cycle blocker will cause a greater proportion of cells at the treatment site to synchronize at the G2/M or M phases where the nuclear membrane is dissolved, whereupon exogenous nucleic acids in the cytosol will be captured within the newly forming nuclear membrane immediately after the nuclear division step. Thus, the exogenous nucleic acids spend a reduced amount of time outside of the nucleus before they are transcribed.

The goal of pretreatment with a cell cycle blocker is to cause a greater proportion of cells at the treatment site (i.e., tumor or other tissue) to be synchronized at the G2/M or M phases. Preferably at least 30%, more preferably at least 60%, more preferably at least 90%, and most preferably at least 95% of the cells at the treatment site are all in the same stage of the cell cycle after treatment with the cell cycle blocker.

The methods of the present invention will preferably be optimized for each different combination of drug, nucleic acid delivery mechanism and treatment site. The key to the optimization is selection of 1) the proper dosage of the cell cycle blocker (e.g., drug or radiation) and of the therapeutic gene; and 2) the proper interval between administration of the cell cycle blocker and administration of the therapeutic gene. For discussion purposes, it is assumed that the "treatment site" component can be a disease indication, such as a neoplasia, or an organ which will benefit from transformation (such as the spleen) to which the drug and the nucleic acid can be administered separately, i.e., by themselves. The optimization relates to the timing and dosages of these separate administrations.

The following dynamic factors are involved in the selection of the proper timing and dosage of the administrations:

1) Drug accumulation at the treatment site in order to initiate the cell cycle block is governed by the properties of the composition, such as its circulation lifetime, uptake rate, etc. This lead time will influence the total time required to obtain maximum synchronization of cells. Exemplary cell cycle blockers are set out in Table I, infra. Radiation is delivered instantaneously, but the period required for the cells to accumulate at G2/M can be determined by a simple time course experiment;

2) Metabolism of the drug and release of the cell from the cell cycle block. Different cell cycle blockers block cells at different stages and will have different synchronizing capabilities. While not intending to be bound by any theory, it is thought that improved expression will be highest when the transfection takes place immediately prior to reconstitution of the nuclear membrane. This suggests that a cell cycle blocker that inhibits the cell cycle at a stage other than M or G2/M can also be used if the intracellular delivery of the nucleic acid is timed to coincide with progression to the M or G2/M phase after release of the cell cycle block. The preferred timing can be confirmed by simple experimentation; and 3) Rate of delivery of nucleic acid. Direct injection to the treatment site presents nucleic acid immediately, although uptake by cells can be accelerated or delayed depending on the carrier (cationic lipid, other transfection additives, buffer alone, etc.). Nucleic acids administered locally or regionally (such as viral delivery or cationic complexes) and systemically (such as with intravenously delivered fully lipid encapsulated SPLPs described herein) have their own characteristic accumulation and transfection rates. A nucleic acid with a long lag time between administration and accumulation may have to be administered at the same time as the cell cycle blocker or, indeed, in advance of the cell cycle blocker.

All known factors for optimization can be characterized by those skilled in the art with a minimum of experimentation. Nonetheless, it has been discovered that the proper interval between administration of the cell blocking agent and administration of the therapeutic nucleic acid governs the synergistic effect between the two components.

The actual combination of drugs and therapeutic genes employed can be selected using considerations similar to those used for combination chemotherapy employing conventional drugs, which is a well known technique of treating cancer. The methods of the present invention have the following advantages: 1) they avoid single agent resistance; 2) in a heterogenous tumor population, the methods can kill cells by different mechanisms; and 3) by selecting drugs with non-overlapping toxicities, each agent used in the methods can be used at frill dose. Some considerations that are well known in selecting drug combinations are as follows:

1) Kinetic considerations: A heterogenous tumor can be treated first with non-cell cycle specific agents (e.g., cyclophosphamide and doxorubicin) to recruit slowly dividing cells into active DNA synthesis; followed by a cell cycle specific drug, such as methotrexate and 5-FU. The drug cycle is repeated at regular intervals.
2) Drug Resistance Considerations: Two or more non-cross-resistant drugs can be used simultaneously to avoid selection of resistant tumor cells. Double resistant mutants may arise by sequential chemotherapy.
3) Drug Interactions: Some combinations (i.e., methotrexate and 5-FU) are synergistic when given in the proper sequence, antagonistic when the order is reversed. Some combinations (i.e., L-Aparaginase and methotrexate) are antagonistic initially, but after an extended period (about 10 days) tumor cells are found to be more sensitive to methotrexate.

The treatment site for the combination therapy, when applied in vivo, refers to the site of a disease or disorder which when directly treated by a therapeutic nucleic acid results in a therapeutic benefit for the patient; alternatively, the treatment site can be an organ or normal cell of the body which when directly treated by a therapeutic nucleic acid results in a therapeutic benefit for the patient. Used in this way, therapeutic benefit refers to an objective or subjective evaluation of a patient of improvement in health. Treatment sites that are not disease sites can include organs such as the spleen, liver, lung or kidney. Useful treatment sites can also include cells of the immune system, tissues with secretory ability, tissues with unique transcription promoters that are highly specific for promoter sequences on the plasmid construct, and the like.

Another important aspect of the invention is that dosages of cell cycle blocking agent will be carefully optimized for each treatment combination and disease indication. Whether the cell cycle blocker is a drug or some form of radiation, the methods of the invention allow for the use of either a therapeutic or a subtherapeutic dose of the cell cycle blocker. In theory, a therapeutic dose falls in the window of dose ranges below unacceptable toxicity and above detectable therapeutic efficacy. A subtherapeutic dose is one which is insufficient to obtain a detectable therapeutic effect. Either dosage is acceptable for use in the methods of the present invention provided the dosage effectively synchronizes cells at the treatment site.

Cells that are effectively synchronized using either a therapeutic or a subtherapeutic dosage are suitable for enhanced transformation. In a typical embodiment, if a therapeutic dosage of the cell cycle blacker vincristine is employed against a human solid tumor, the cells at the tumor site fall into one of the following three categories: (1) those exposed to a cell killing amount of drug; (2) those exposed to a cell cycle blocking amount of drug (which block is removed once the drug is metabolized); and (3) cells which do not contact sufficient drug to be affected. It is the cells in the second category that the subsequent treatment with the therapeutic nucleic acid will enhance, given that the cells in the fast category are killed and the cells in the third category are not synchronized. If a subtherapeutic dosage of vincristine were employed in the same model, only two cell populations would result, i.e., (2) and (3). Again, cells in the second category will demonstrate enhanced transformation with subsequently administered therapeutic nucleic acids. The methods of the invention, therefore, allows for the use of either a therapeutic or a subtherapeutic dosage of cell blocking agent. Further, the methods of the present invention allow for the use of new drugs that were previously unacceptable because of high toxicity at therapeutic levels.

In addition to the foregoing, it is pointed out that in a normal tumor, there exists a significant fraction of quiescent cells which are not amenable to cell cycle modulators or lipid transfection reagents. However, if the cell cycle modulating agent arrests cells irreversibly leading to localized regions of cell death, the previously quiescent cells surrounding these regions now begin to divide and repopulate the regions of cell death. Thus, the repopulating cells are now amenable to cell cycle modulation for improvement in transfection.

TABLE 1

| Drug | Cell Cycle Blocking Stage | Mode of Action |
| --- | --- | --- |
| 5-fluorouracil | S | Effects DNA/RNA synthesis |
| Aphidicolin | G1/S | (Unknown) |
| Camptothecin | G2/M | Binds to TOPO I |
| Cisplatin | S (Unknown) | Causes intra/inter strand cross linking of DNA |
| Colchicine | (Unknown) | Prevents endosome/lysosome fusion |
| Cyclophosphamide | (Unknown) | Alkylating agent |
| Daunorubicin | S (Unknown) | Binds to DNA/RNA |
| Dexamethosone | G1 | (Unknown) |
| DTIC (Dacarbazine) | S | purine analogue/alkylating agent |
| Doxorubicin (Adriamycin) | S | Binds to DNA/inhibits protein synthesis |
| Etoposide | G2/M | Binds to TOPO II |
| Fludarbine | S | Inhibition of ribonucleotide reductase and DNA pol α |
| Hydroxyurea | S | (Unknown) |
| Ifosfamide | G1 | DNA-DNA crosslinks |
| Methotrexate | S | Inhibits DHFR |
| Taxol (Paclitaxel/Docetaxel) | G2/M | Prevents depolymerization of microtubules |
| Vinblastine | G2/M | S and G2/M (inhibits cell energy mechanism) |
| Vincristine | G2/M | prevents microtubule formation |
| Vinorelbine (Navelbine) | G2/M | Interacts with tubulin |

D. Delivery of Foreign Therapeutic Genes

Techniques for in vivo delivery of foreign therapeutic genes can be divided into two classes: (1) those preferred for local or regional delivery (i.e., by inhalation, or direct injection), and (2) those preferred for systemic delivery (i.e., intravenous delivery). According to the methods of the instant invention, either technique can be enhanced by pretreating the cells at the treatment site with a cell cycle blocking agent.

Techniques for in vivo delivery of foreign therapeutic genes are known to those skilled in the art, and are the focus of over 200 FDA approved clinical trials. The following outline serves only to summarize information on the techniques that are widely available. Incorporated herein by reference are Zhu, et al., *Science* 261:209–211(1993), which describes the intravenous delivery of cytomegalovirus (CMV)-chloramphenicol acetyltransferase (CAT) expression plasmid using DOTMA-DOPE complexes; Hyde, et al., *Nature* 362:250–256 (1993), which describes the delivery of the cystic fibrosis transmembrane conductance regulator (CFTR) gene to epithelia of the airway and to alveoli in the lung of mice, using liposomes; and Brigham, et al., *Am. J. Med. Sci.* 298:278–281 (1989), which describes the in vivo transfection of lungs of mice with a functioning prokaryotic gene encoding the intracellular enzyme chloramphenicol acetyltransferase (CAT).

1. Generating Plasmid Expression Constructs of Therapeutic Genes

The cloning and expression of natural or synthetic nucleic acids is typically achieved by operably linking a nucleic acid of interest to a promoter (which is either constitutive or inducible), incorporating the construct into an expression vector and introducing the vector into a suitable host cell. Typical vectors contain transcription and translation terminators, transcription and translation initiation sequences and promoters useful for regulation of the expression of the particular nucleic acid. The vectors optionally comprise generic expression cassettes containing at least one independent terminator sequence, sequences permitting replication of the cassette in eukaryotes, prokaryotes or both, (e.g., shuttle vectors) and selection markers for both prokaryotic and eukaryotic systems. Vectors are suitable for replication and integration in prokaryotes, eukaryotes or preferably both. See, Giliman and Smith, *Gene*, 8:81–97 (1979); Roberts, et al., *Nature*, 328:731–734 (1987); Berger and Kimmel, Guide to Molecular Cloning Techniques, *Methods in Enzymology* 152, Academic Press, Inc., San Diego, Calif. (Berger); Sambrook, et al. (1989), *Molecular Cloning—A Laboratory Manual* (2nd ed.) Vol. 1–3, Cold Spring Harbor Laboratory, Cold Spring Harbor Press, NY, (Sambrook); and F. M. Ausubel, et al., *Current Protocols in Molecular Biology*, eds., Current Protocols, a joint venture between Greene Publishing Associates, Inc. and John Wiley & Sons, Inc., (1994 Supplement) (Ausubel). Product information from manufacturers of biological reagents and experimental equipment also provide information useful in known biological methods. Such manufacturers include the SIGMA chemical company (Saint Louis, Mo.), R&D systems (Minneapolis, Minn.), Pharmacia LKB Biotechnology (Piscataway, N.J.), CLONTECH Laboratories, Inc. (Palo Alto, Calif.), Chem Genes Corp., Aldrich Chemical Company (Milwaukee, (Wis.), Glen Research, Inc., GIBCO BRL Life Technologies, Inc. (Gaithersberg, Md.), Fluka Chemica-Biochemika Analytika (Fluka Chemie AG, Bucks, Switzerland), and Applied Biosystems (Foster City, Calif.), as well as many other commercial sources known to one of skill.

2. Viral Vector Systems for Therapeutic Genes

A number of vector systems can be used to express the nucleic acids used in the methods of the present invention. These include plasmids, cosmids and a number of viral vectors, including retroviral vectors, vaccinia vectors, lentiviral vectors, herpes simplex vectors, Sindbis/semliki forest viruses, adenoviral vectors, and adeno-associated viral (AAV) vectors. Each vector system has advantages and disadvantages that relate to host cell range, intracellular location, level and duration of transgene expression and ease of scale-up/purification. Optimal viral delivery systems are characterized by: (1) broad host range; (2) high titer/$\mu$g DNA; (3) stable expression; (4) non-toxic to host cells; (5) no replication in host cells; (6) ideally no viral gene expression; (7) stable transmission to daughter cells; (8) high rescue yield; and (9) lack of subsequent replication-competent virus that may interfere with subsequent analysis. Choice of vector may depend on the intended application. Preparation of retroviral vectors and their uses are described in many publications including European Patent Application 0 178 220, U.S. Pat. No. 4,405,712; Gilboa, *Biotechniques*, 4:504–512 (1986), Mann, et al., *Cell*, 33:153–159 (1983); Cone and Mulligan, *Proc. Natl. Acad. Sci. USA*, 81:6349–6353 (1984), Eglitis, et al., *Biotechniques*, 6:608–614 (1988); Miller, et al., *Biotechniques*, 7:981–990 (1989); Miller, A. D. *Nature, supra* (1992); Mulligan, R. C., supra (1993); and Gould, et al. and PCT Publication No. WO 92/07943 entitled "Retroviral Vectors Useful in Gene Therapy," all of which are incorporated herein by reference.

3The Stable Plasmid-lipid Particles ("SPLPs")

A preferred method for transforming cells involves the use of lipid-nucleic acid particles. Preferred/compositions and methods of making such particles are generally described in U.S. Pat. No. 5,705,385 and U.S. patent applications Ser. Nos. 08/485,458, 08/660,025, 08/484,282, 08/316,399, PCT Publication No. WO 9640964, and Provisional patent application Ser. No. 60/073,598, all of which are assigned to the assignee of the instant invention and are incorporated herein by reference.

It is often desirable to include a steric barrier compound, such as ATTA-lipids; polyethylene glycol (PEG)-lipid derivatives (e.g., PEG-ceramides) or ganglioside $G_{M1}$-modified lipids, in the lipid-nucleic acid particles used in the methods of the present invention. Addition of such components prevents particle aggregation and provides a means for increasing the circulation lifetime and increasing the delivery of the lipid-nucleic acid particles to the target tissues of interest. Typically, the concentration of the steric barrier compound (e.g., ATTA-lipid, PEG-ceramide or $G_{M1}$-modified lipids) in the lipid-nucleic acid particle will range from about 1% to about 20%.

Overall particle charge is also an important determinant in particle clearance from the blood, with negatively charged complexes being taken up more rapidly by the reticuloendothelial system (see, Juliano, *Biochem. Biophys. Res. Common.*, 63:651 (1975)) and, thus, having shorter half-lives in the bloodstream. Particles with prolonged circulation half-lives are typically desirable for therapeutic and diagnostic uses. For instance, particles which can be maintained from 8, 12, or up to 24 hours in the bloodstream are particularly preferred.

Particular formulations of SPLPs that are presently preferred for use in the methods of the present invention are set out in the Example Section.

4, Direct Injection of Lipid-nucleic Acid Complexes or Naked DNA

Other methods known in the art for delivering a therapeutic gene to a treatment site are direct injection to the treatment site (local or regional) of lipid-nucleic acid complexes or naked DNA. Disclosure of techniques for cationic lipid-plasmid aggregates (complexes or "lipoplexes") are found in Nabel, et al., "Methods for Liposome-Mediated Gene Transfer to Tumor Cells in Vivo," Chapter 21, *Methods in Molecular Medicine*, (Ed. P. Robbins, 1997. Humana Press Inc., Totowa, N.J.; and Son, et al., "Cationic Liposome: Mediated Gene Transfer to Tumor Cells in Vitro and In Vivo," Chapter 23, *Methods in Molecular Medicine*, supra. Techniques for delivery of naked DNA are disclosed, for example, in U.S. Pat No. 5,589,466, which issued to Felgner, et al., and U.S. Pat. No. 5,676,954, which issued to Brigham and which sets out a method of delivering lipid-DNA complexes by direct injection to an immediately adjacent capillary bed.

5. In vitro Gene Transfer

The methods of the invention are also useful for enhanced efficiency of delivery of a therapeutic gene to cells in vitro. It is expected that those of skill in the art are knowledgeable in the numerous expression systems available for expression of DNA. No attempt to describe in detail the various methods known for the expression of proteins in prokaryotes or eukaryotes is made here. There are several well-known methods of introducing nucleic acids into bacterial and animal cells, any of which may be used in the present invention. These include, but are not limited to, calcium phosphate precipitation, fusion of the recipient cells with bacterial protoplasts containing the DNA, treatment of the recipient cells with liposomes containing the DNA, DEAE damn, receptor-mediated endocytosis, electroporation, micro-injection of the DNA directly into the cells, infection with viral vectors, etc. Currently preferred methods are by cationic lipid/plasmid aggregates (see, U.S. Pat. No. 5,591,601, which issued to Wegner, et al.), or by systemic delivery through a circulatory system using an encapsulated, nuclease resistant lipid-DNA particle. Particularly preferred methods of encapsulating DNA for systemic delivery are disclosed in U.S. Pat. No. 5,705,385 and U.S. patent applications Ser. Nos. 08/485,458, 08/660,025, 08/484,282 and PCT Publication No. WO 96/40964, and Provisional Patent Application Ser. No. 60/073,598, all of which are assigned to the assignee of the instant invention and are incorporated herein by reference. Transformation of tumor cells is also accomplished by injection of naked DNA directly into a target cell or target tumor cell mass (see, U.S. Pat. Nos. 5,580,859 and 5,589,466, both of which issued to Felgner, et al.).

For in vitro applications, the delivery of nucleic acids can be to any cell grown in culture, whether of bacterial, plant or animal origin, vertebrate or invertebrate, and of any tissue or type. Contact between the cells and the genetically engineered nucleic acid constructs, when carried out in vitro, takes place in a biologically compatible medium. The concentration of nucleic acid varies widely depending on the particular application, but is generally between about 1 $\mu$mol and about 10 mmol. Treatment of the cells with the nucleic acid is generally carried out at physiological temperatures (about 37° C.) for periods of time ranging from about 1 to about 48 hours, preferably from about 2 to about 4 hours.

The lipid-nucleic acid particles of the present invention can be adsorbed to almost any cell type. Once adsorbed, the particles can either be endocytosed by a portion of the cells, exchange lipids with cell membranes or fuse with the cells. Transfer or incorporation of the nucleic acid portion of the particle can take place via any one of these pathways. In particular, when fusion takes place, the particle membrane is integrated into the cell membrane and the contents of the particle combine with the intracellular fluid. Contact between the cells and the lipid-nucleic acid particles, when carried out in vitro, will take place in a biologically compatible medium. The concentration of particles can vary widely depending on the particular application, but is generally between about 1 $\mu$mol and about 10 mmol. Treatment of the cells with the lipid nucleic acid particles will generally be carried out at physiological temperatures (about 37° C.) for periods of time ranging from about 1 to about 6 hours and, more preferably, from about 2 to about 4 hours. For in vitro applications, the delivery of nucleic acids can be to any cell grown in culture, whether of plant or animal origin, vertebrate or invertebrate, and of any tissue or type. In preferred embodiments, the cells will be animal cells, more preferably mammalian cells, and most preferably human cells.

In one group of preferred embodiments, a lipid-nucleic acid particle suspension is added to 60–80% confluent plated cells having a cell density of from about $10^3$ to about $10^5$ cells/mL and, more preferably, from about $2\times10^4$ cells/mL. The concentration of the suspension added to the cells is preferably from about 0.01 to 0.2 $\mu$g/mL and, more preferably, about 0.1 $\mu$g/mL.

E. Administration of the Therapeutic Nucleic Acid Formulation

The nucleic acids (for example, SPLPs) of the present invention are administered either alone or in mixture with a physiologically-acceptable carrier (such as physiological saline or phosphate buffer) selected in accordance with the route of administration and standard pharmaceutical practice. Generally, normal saline will be employed as the pharmaceutically acceptable carrier. Other suitable carriers include, e.g., water, buffered water, 0.4% saline, 0.3% glycine and the like, including glycoproteins for enhanced stability, such as albumin, lipoprotein, globulin, etc. These compositions may be sterilized by conventional, well known sterilization techniques. The resulting aqueous solutions may be packaged for use or filtered under aseptic conditions and lyophilized, the lyophilized preparation being combined with a sterile aqueous solution prior to administration. The compositions may contain pharmaceutically acceptable auxiliary substances as required to approximate physiological conditions, such as pH adjusting and buffering agents, tonicity adjusting agents and the like, for example, sodium acetate, sodium lactate, sodium chloride, potassium chloride, calcium chloride, etc. Additionally, the particle suspension may include lipid-protective agents which protect lipids against free-radical and lipid-peroxidative damages on storage. Lipophilic free-radical quenchers, such as alphatocopherol and water-soluble iron-specific chelators, such as ferrioxamine, are suitable. Formulations suitable for administration include aqueous and man-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations of packaged nucleic acid can be presented in unit-dose or multi-dose sealed containers, such as ampules and vials. Injection solutions and suspensions can be prepared from sterile powders, granules, and tablets of the kind previously described.

Lipid-nucleic acid particles can be incorporated into a broad range of topical dosage forms including, but not limited to, gels, oils, emulsions and the like. The suspension containing the lipid-nucleic acid particles can be formulated and administered as topical creams, pastes, ointments, gels, lotions and the like.

The concentration of particles in the pharmaceutical formulations can vary widely, i.e., from less than about 0.05%, usually at or at least about 2–5% to as much as 10 to 30% by weight and will be selected primarily by fluid volumes, viscosities, etc., in accordance with the particular mode of administration selected. For example, the concentration may be increased to lower the fluid load associated with treatment. This may be particularly desirable in patients having atherosclerosis-associated congestive heart failure or severe hypertension. Alternatively, particles composed of irritating lipids may be diluted to low concentrations to lessen inflammation at the site of administration. For diagnosis, the amount of particles administered will depend on the particular label used, the disease state being diagnosed and the judgment of the clinician, but will generally be between about 0.01 and about 50 mg per kilogram of body weight, preferably between about 0.1 and about 5 mg/kg of body weight.

For in vivo administration, pharmaceutical compositions that comprise the cell cycle synchronizers and/or nucleic acids of the invention are preferably administered parentally, i.e., intraarticularly, intravenously, intraperitoneally, subcutaneously, or intramuscularly. More preferably, the pharmaceutical compositions are systemically administered intravenously or intraperitoneally by a bolus injection. For example, see Stadler, et al., U.S. Pat. No. 5,286,634, which is incorporated herein by reference. Intracellular nucleic acid delivery has also been discussed in Straubringer, et al., *Methods in Enzymology*, Academic Press, New York, 101:512–527 (1983); Mannino, et al., *Biotechniques*, 6:682–690 (1988); Nicolau, et al., *Crit. Rev. Ther. Drug Carrier Syst.*, 6:239–271 (1989), and Behr, *Acc. Chem. Res.*, 26:274–278 (1993). Still other methods of administering therapeutics are described in, for example, Rahman, et al., U.S. Pat. No. 3,993,754; Sears, U.S. Pat. No. 4,145,410; Papahadjopoulos, et al., U.S. Pat. No. 4,235,871; Schneider, U.S. Pat. No. 4,224,179; Lenk, et al., U.S. Pat. No. 4,522,803; and Fountain, et al., U.S. Pat. No. 4,588,578.

In preferred embodiments, the pharmaceutical preparations may be contacted with the target tissue by direct application of the preparation to the tissue. The application may be made by topical, "open" or "closed" procedures. By "topical" it is meant the direct application of the pharmaceutical preparation to a tissue exposed to the environment, such as the skin, oropharynx, external auditory canal, and the like. "Open" procedures are those procedures which include incising the skin of a patient and directly visualizing the underlying tissue to which the pharmaceutical preparations are applied. This is generally accomplished by a surgical procedure, such as a thoracotomy to access the lungs, abdominal laparotomy to access abdominal viscera, or other direct surgical approach to the target tissue. "Closed" procedures are invasive procedures in which the internal target tissues are not directly visualized, but accessed via inserting instruments through small wounds in the skin. For example, the preparations may be administered to the peritoneum by needle lavage. Likewise, the preparations may be administered through endoscopic devices.

The nucleic acid can also be administered in an aerosol inhaled into the lungs (see, Brigham, et al., *Am. J. Sci.* 298(4):278–281 (1989)), or by direct injection at the site of disease (see, Culver, *Human Gene Therapy*, MaryAnn Liebert, Inc., Publishers, New York, pp. 70–71 (1994)).

In some embodiments, the particles and/or compositions comprising the particles will have a targeting moiety attached to the surface of the particle. Methods of attaching targeting moieties (e.g., antibodies, proteins) to lipids (such as those used in the present particles) are known to those of skill in the art.

Effective doses of the compositions of the present invention will vary depending upon many different factors, including means of administration, target site, physiological state of the patient, and other medicants administered. Thus, treatment dosages will need to be titrated to optimize safety and efficacy. In determining the effective amount of the therapeutic gene formulation to be administered, the physician evaluates the particular nucleic acid used; the disease state being diagnosed; the age, weight, and condition of the patient; circulating plasma levels; vector toxicities; progression of the disease; and the production of anti-vector antibodies. The size of the dose also will be determined by the existence, nature, and extent of any adverse side-effects that accompany the administration of a particular vector. For systemic delivery of therapeutic genes, e.g., SPLPs, doses ranging from about 10 ng to 1 g and, more preferable, from about 100 ng to 750 mg DNA per human patient are typical. Doses generally range between about 0.01 and about 50 mg per kilogram of body weight when delivered intravenously; preferably between about 0.1 and about 20 mg/kg of body weight or about $10^8$–$10^{10}$ or $10^{12}$ particles per injection. In general, the dose equivalent of a naked nucleic acid from a vector is from about 100 g to 750 mg for a typical 70 kilogram patient, and doses of vectors which include a retroviral particle are calculated to yield an equivalent amount of inhibitor nucleic acid. Proper dosage can be determined by those skilled in the art based on a simple dose ranging study.

The dosage of therapeutic gene will be influenced by the formulation and method of delivery. Naked DNA or lipid-DNA complexes which are not suitable for systemic delivery may be given by direct injection. In this case, a DNA dosage of about 0.1–100 $\mu$g per injection site is useful; however, toxic amounts of cationic-lipid complexes must be avoided.

For systemic delivery of lipid-DNA particles, such as SPLPs, it is known that a lipid amounts of 50–150 mg/kg are preferred with 100 mg/kg being most preferable. Thus, a suitable dosage of SPLPs for a typical 70 kg patient will be approximately 7 g lipid. Since SPLPs can be formulated with a wide variety of drug to lipid ratios (i.e. <1 to 25% by weight DNA), the total DNA administered to the patient can be varied from <70 to about 1750 mg DNA. Doses of lipid below the recommended amounts may be used, but they tend to be more rapidly cleared from blood. Those skilled in the art can determine the proper amount of an SPLP of a suitable drug:lipid ratio based on elementary experimentation, using the principles disclosed herein.

Prior to infusion, blood samples are obtained and saved for analysis. Between $10^8$ and $1\times10^{12}$ vectors are infused intravenously over 60–200 minutes. Vital signs and oxygen saturation by pulse oximetry are closely monitored. Blood samples are obtained 5 minutes and 1 hour following infusion and saved for subsequent analysis. At the physician's discretion, reinfusion is repeated about every 2 to 3 months for a total of about 4 to 6 treatments in a one year period. After the first treatment, infusions can be performed on an outpatient basis at the discretion of the clinician. If the reinfusion is given as an outpatient, the participant is monitored for at least about 4 and, preferably, about 8 hours following the therapy.

If a patient undergoing infusion of a vector or transduced cell develops fevers, chills, or muscle aches, he/she receives the appropriate dose of aspirin, ibuprofen or acetaminophen. Patients who experience reactions to the infusion, such as fever, muscle aches, and chills, are premedicated 30 minutes prior to the future infusions with either aspirin, acetaminophen or diphenhydramine. Meperidine is used for more severe chills and muscle aches that do not quickly respond to antipyretics and antihistamines. Vector infusion is slowed or discontinued depending upon the severity of the reaction.

In vivo gene transfer using the methods of the present invention can be practiced in a variety of hosts. Preferred hosts include mammalian species, such as humans, nonhuman primates, dogs, cats, cattle, horses, sheep, and the like.

The present invention also provides synchronizing compounds (including cell cycle blockers) and lipid-nucleic acid particles in kit form. The kit will typically be comprised of a container which is compartmentalized for holding the various elements of the kit. The kit will contain the compositions of the present inventions, preferably in dehydrated form, with instructions for their rehydration and administration.

6. Transformation Efficiency

Improvements in the transformation efficiency that are obtained using the invention of the present application can be determined in a variety of ways known to those skilled in the art. Two ways, discussed below, are (1) improvement in therapeutic benefit as determined by subjective or objective observation of the patient; and (2) improvement in desired phenotypic change at the physiological or molecular level.

Improvements in transformation efficiency that result in therapeutic benefit means generally a result where, if the mammal is human, the patient may note improved vigor or vitality or decreased pain as subjective symptoms of improvement or response to therapy. Alternatively, the clinician may notice a decrease in disease or disorder, or the symptoms of disease or disorder, such as reduced tumor size or tumor burden based on physical exam, laboratory parameters, tumor markers, or radiographic findings.

Transformation efficiency is also demonstrated by improvement of the phenotype at the molecular level. This improvement may be ascertained by detection and quantification of the presence and expression of nucleic acids and their gene products at the treatment site. The nucleic acids used in the present invention, and their gene products, are detected and quantified by any of a number of means well known to those of skill in the art. A general summary of these means includes analytic biochemical methods, such as spectrophotometry, radiography, electrophoresis, capillary electrophoresis, high performance liquid chromatography (HPLC), thin layer chromatography (TLC), hyperdiffusion chromatography and the like, and various immunological methods, such as fluid or gel precipitin reactions, immunodiffusion (single or double), immunoelectrophoresis, radioimmunoassays (RIAs), enzyme-linked immunosorbent assays (ELISAs), immunofluorescent assays and the like. The detection of nucleic acids proceeds by well known methods such as Southern analysis, northern analysis, gel electrophoresis, PCR, radiolabeling, scintillation counting and affinity chromatography.

A general source for detection of nucleic acids is Sambrook, et al.; *Nucleic Acid Hybridization, A practical Approach*, Ed. Flames, B. D., et al., IRL Press (1985). For detection of gene products, the above-described hybridization methods can be used where the gene product is a nucleic acid. Preferred methods for detecting protein gene products involve the use of specific antibodies (see, e.g., Coligan, *Current Protocols in Immunology*, Wiley/Greene, NY (1991); and Harlow and Lane (1989), *Antibodies: A Laboratory Manual*, Cold Spring Harbor Press, NY; Stites, et al., (eds.) *Basic and Clinical Immunology* (4th ed.) Lange Medical Publications, Los Altos, Calif., and references cited therein; and Goding (1986), *Monoclonal Antibodies: Principles and Practice* (2d ed.) Academic Press, New York, N.Y.).

The following examples set out specific embodiments of the invention which further set forth how the invention is to be practiced. The following examples are offered to illustrate, but not to limit the present invention.

EXAMPLES

1. Materials

Plasmids are preferably supercoiled, 4000 to 15000 bp in length, encoding genes and enhancer elements, etc. as desired. Cationic lipid, N,N-dioleyl-N,N-dimethyl ammonium chloride ("DODAC") and monomethoxy polyethylene2000 glycol succinate-(C8:0-ceramide) ("PEG-Cer-C8") were synthesized at Inex Pharmaceuticals Corp. Dioleylphosphatidylethanolamine (DOPE) was supplied by Northern Lipids, Vancouver. Standard dialysis membranes: Spectro/Por 5 regenerated Cellulose (12–14,000 MWCO) was purchased from VWR (Manufactured by Spectrum Medical Industries Inc.). Sodium Citrate was purchased from BDH. Sodium Chloride, Triton X-100 and Octyl-beta-D-glucopyranoside ("OGP") were obtained from VWR Scientific, Fisher Scientific or Sigma Chemical Company.

2. The Formulations a. Formulation 1.1 also Known as INEX 301

Plasmid (50–400 $\mu$g) is incubated with DODAC in 500 $\mu$L of the prep solution containing 0.2 M OGP in 150 mM NaCl; 5 mM HEPES pH 7.4, for 30 min at room temperature. This mixture is added to a mixture of DOPE and PEG-Cer-C14 or PEG-Cer-C20 or PEG-Cer-C8 in 500 $\mu$L of the same prep solution. The total lipid concentration was either 5 or 10 mg/mL, with the molar ratio of DOPE:DODAC:PEG-Cer being 84:6:10. The mixture was dialyzed against 150 mM NaCl; 5 mM HEPES (pH 7.4) for 36–48 h with two buffer changes.

Nonencapsulated DNA was removed by anion exchange chromatography on DEAE-Sepharose column (1×4 cm). Empty liposomes were removed by pooling lipid/DNA samples that co-eluted on the DEAE column on top of a sucrose density gradient in 12.5 mL ultracentrifuge tubes. The gradient was formed with 3 mL each of 10% sucrose, 2.5% sucrose and 1% sucrose in HBS layered consecutively from bottom to top. The gradients were centrifuged at 36,000 rpm (160,000×g) for 2 h at 20° C. in a Beckman Optima XL-100K ultracentrifuge using an SW-28 rotor. Separated bands were removed from top to bottom. Fractions were assayed for $^3$H-plasmid and $^{14}$C-CHE by dual-label scintillation counting using a Beckman LS6500 scintillation counter. The lipid encapsulated plasmid DNA banded tightly at the interface between 2.5% and 10% sucrose, while the unassociated lipid was present as a smear from the top of the gradient to the interface between 1% and 2.5% sucrose. The formulation can be concentrated in 12–14,000 MWCO dialysis tubing against 500,000 MW PEG (Aquacide II). When the desired volume is reached, the formulation was transferred into a new dialysis bag and dialyzed overnight against HBS to adjust the NaCl concentration to 150 mM.

b. Formulation 1.2 also Known as INEX 351

In Formulation 1.2, the following concentrations were used: lipid concentration: 5.0 mg/mL (or 5.3 mM); plasmid concentration: 200 $\mu$g; initial volume: 1.0 mL; and lipid stock solutions: (in 95:5 benzene:methanol, 2:1 chloroform:methanol or ethanol). Calculated by molarity (dissolved in 95:5 benzene:methanol or 2:1 chloroform:methanol): DOPE (744 g/mol): 40 mM; DODAC (582 g/mol): 40 mM; PEG-C8 (2515 g/mol): 20 mM.

|  | DOPE | DODAC | PEG-C8 |
|---|---|---|---|
| mg | 1.68 | 1.315 | 2.005 |
| mole % | 42.5 | 42.5 | 15 |
| μmol | 2.25 | 2.25 | 0.8 |
| μl | 56.2 | 56.2 | 40 |

The procedure for making the formulation on a 1 mL scale was as follows: Aliquot lipid stock solutions into a clean, dry test tube and dry to a lipid film using a stream of $N_2$ gas and then dry under vacuum for at least 2 hours. Add 50 μL 2M OGP and add 500 μL of 2× strength dialysis buffer, add 200 μg of plasmid and mix by vortexing to dissolve the lipid film. Make up to 1.0 mL with sterile deionized $H_2O$, mix and allow to incubate approximately 30 min. at room temperature. Place the solution into a dialysis bag and dialyze for 40–48 hours against 2 L of dialysis buffer with 1–2 changes of buffer after approximately 24 hours, determine the volume of the sample by weighing in a tarred tube (assume density of 1.0), These steps can be followed by DEAE cleaning and/or sucrose density gradient centrifugation, as described above.

After DEAF cleaning and sucrose density centrifugation, Formulation 1.2 has a concentration of 200 μg/mL plasmid and 5 mg/mL total lipid.

To reduce the cationic surface charge of Formulation 1.2, it is desirable to reduce the amount of cationic lipid (i.e., DODAC) employed. If the amount of DODAC is changed, the amount of DOPE is changed to maintain the same total amount of lipid. Formulations below 30% DODAC are preferably made in 10 mg total lipid. Dialysis buffer can be changed as in Table 2, below:

TABLE 2

Characterization of Representative Large Scale Formulations

| DODAC Conc. | Starting Volume | Buffer | Encapsulation efficiency | Nicomp particle size (nm)[a] |
|---|---|---|---|---|
| 42.5% | 30 mL | 150 mM $NaPO_4$, 130 mM NaCl | 49% | 131 |
| 30% | 12 mL | 150 mM $NaPO_4$ | 56.8% | 109 |
| 24% | 30 mL | 130 mM $NaPO_4$ | 50.7% | 250 |
| 20% | 15 mL | 105 mM $NaPO_4$ | 63% | 178 |

[a]Nicomp analysis of mean particle size, gaussian distribution and volume weighting before DEAE cleaning and isolation.

c. Formulation 1.3 also Known as INEX 324

Lipid-plasmid particles with 10–30% DODAC are also useful in the present invention. These can be formulated as described above or as follows.

Lipid stock solutions: Individual stock solutions of each lipid were dissolved in chloroform/methanol (2:1 v/v) to a final concentration of 2 or 20 mg/mL.

OGP solution: 1.0 M OGP solution was prepared in MilliQ grade water.

Citrate buffer: Sodium citrate buffer was used for dialysis to remove detergent from the formulation. The citrate concentrations were varied according to the amount of DODAC. The buffer also contains 150 mM NaCl and 5 mM HEPES at pH 7.4, unless indicated otherwise. In general, a 10× solution was prepared and diluted 1:10 in MilliQ Plus water for dialysis using a graduated cylinder.

Preparation of lipid/DNA/OGP mixture: A typical formulation contained 10 mg of lipid of DODAC/DOPE/PEG-Cer-C8 and 200 μg DNA. Appropriate amounts of stock solutions containing DODAC, DOPE and PEG-Cer-C8 (normally 15 mol % in this study) were mixed in a glass test tube, If the amount of DODAC is changed, the amount of DOPE is changed to maintain a total of 10 mg lipid. The solvent was first removed under a stream of $N_2$ gas followed by incubation under vacuum for 3–5 h. To the lipid, 0.2 mL of 1 M OGP was added. The suspension was vortexed until the lipid was totally dissolved and the solution became clear. Then a 0.2 mL DNA (1 mg/mL) solution containing 200 μg DNA and 0.6 mL HBS (HEPES buffered saline) or citrate buffer (concentrations designated in FIG. 1) were added to a final total volume of 1 mL. If the solution did not become clear, a small amount of OGP (50 μL) was added. The solution was incubated at room temperature for 1 hr to allow the components to equilibrate.

Dialysis: Dialysis tubes were soaked in 60% ethanol (or in distilled water if sterilization was not required) for 30 min. The mixture of DNA/lipid/OGP solution was then transferred to the dialysis tube. The sample was dialyzed for 2 days in 2–4 L citrate buffer (concentration as described in FIG. 1) with two changes of buffer daily.

After preparation, empty liposomes can be removed by DEAE cleaning and sucrose density centrifugation as described above. Having been taught the various lipid-plasmid particle formulations suitable for systemic delivery in this example, it would be obvious to one skilled in the art to modify them, for example, for improved plasmid delivery and/or intracellular expression using one or more possible variations. Variations of the following type are suggested: percentage of PEG-lipid; size of PEG; length of hydrophobic (anchor) chain; pH sensitive PEG-lipids; replacement of PEG by ATTA (disclosed in U.S. patent application Ser. No. 60/073852, filed Dec. 2, 1997 bearing TTC Attorney Docket No. 16303-005810, which is assigned to the assignee of the instant invention and incorporated herein by reference); addition of membrane modifying lipids, such as cholesterol or DOPE; use of alternative cationic lipids, such as DMRIE, DOTAP, DOTMA, DODMA, AL-1, etc.; use of fusogenic components, such as pH sensitive lipids, peptides (EALA) SEQ ID NO:2 polymers (PEAA); use of targeting agents; use of DNA condensing peptides (i.e., polylysine or spermine) or polymers (i.e., PEI); use of negatively charged lipids, such as phosphatidylserine; or use of alternative PEG-lipid linkers, such as SPDPs or PDPH (disclosed in U.S. patent application Ser. No. 08/536,584, which is assigned to assignee of the instant invention).

d. Formulation 1.4 also Known as INEX 303

Formulation 1.4 contains DOPE:DODAC:PEG-Cer-C20 (83:7:10) mol %. The synthesis protocol is as follows: Aliquot the lipid stock solutions (in ethanol) into an autoclaved, clean, dry round bottom flask. The solution is dried to a lipid film using a rotavap in a 65° C. water bath and vacuumed overnight. Add HBS with octylglucopyranoside (OGP) to a final OGP concentration of 200 mM. Swirl the mixture to dissolve the lipid film and, if necessary, heat to 37° C. to ensure the lipid is fully dissolved. Plasmid DNA is then added (400 μg/10 mg lipid) to the dissolved lipid films. After incubation at room temperature for 30 minutes, place the resulting solution in a dialysis bag that has been pre-soaked in filter sterilized distilled $H_2O$ and autoclaved. Dialyze overnight against 20 L of dialysis buffer (5 mM HEPES, 150 mM NaCl, pH 7.4, filter sterilized through a 0.2 micron sterile filter) with two buffer changes.

Nonencapsulated DNA was removed by anion exchange chromatography on a DEAE-Sepharose CL-6B column. Collect the particle suspension as it appears in the eluate, and concentrate using the Amicon diafiltration system (YM 30 membrane). Next, empty liposomes were removed using a sucrose density gradient. The gradient was formed by layering 10% sucrose, 5.0% sucrose and 2.5% sucrose in HBS, pH 7.4. The sample is loaded by floating it on top of the 2.5% sucrose layer and centrifuging at 28,000 rpm for 18 hours at 20° C. using a Beckman Optima XL-100K ultracentrifuge and an SW-28 rotor. After centrifugation, remove the lower band with a syringe and needle and pool the samples. The sucrose is removed and the sample is concentrated simultaneously using the Amicon system. Filter sterilize the final volume through a 0.2 micron filter. DNA concentration is analyzed using, for example, Picogreen assays; lipid concentration is analyzed using, for example, HPLC; and particle size is analyzed using, for example, Nicomp analysis.

e. Formulation 1.5 also Known as "Ethanol Method"

This method is an alternative high-efficiency formulation of the lipid/nucleic acid particle. This method is disclosed in PCT Patent Publication No. WO 96/40964, the teachings of which are incorporated herein by reference. It is, in essence, a preparation of lipid therapeutic nucleic acid particles in organic solvent. The following stock solutions of lipid are prepared in 100% ethanol: DSPC: 20 mg/mL (20 mol %)=128.4 µL; Chol.: 20 mg/mL (25 mol %)=113.1 µL; DODAP: 40 mg/mL (45 mol %)=44.5 µl; PEG-Cer-C20 (or C14): 50 mg/mL (10 mol %)=67.6 µL.

The lipids are mixed together and the volume is increased to a total volume of 0.400 mL with 100% ethanol. An appropriate volume of 300 mM citrate buffer (pH 3.3) is added to the DNA to a final volume of 600 µL and pH 3.8. Warm the two solutions to 65° C. for 2 minutes. While vortexing the DNA tube, use a Pasteur pipette to add lipid (in ethanol) in a dropwise manner to the DNA solution. The resulting solution will get cloudy and can bubble, but no aggregates should be present. Place the solution in presoaked dialysis tubing (12–14,000 MWCO) and dialyze for 1 hour against 300 mM citrate buffer (pH 3.7–4.0). Transfer the dialysis tubing to HBS (pH 7.5) and dialyze for 12 hours. Nonencapsulated DNA was removed by anion exchange chromatography using a DEAF-sepharose column equilibrated in HBS. If necessary, the final preparation can be concentrated using the Amicon system (YM 30 membrane). DNA concentration is analyzed using, for example, Picogreen assays, whereas the lipid concentration is analyzed using, for example, HPLC.

3. Materials and Methods a. Cells Culture

SK-OV-3 cells (human ovarian tumor cells, ATCC) were cultured in RPMI 1640 media (StemCell Technologies, Vancouver, B.C.) supplemented with 10% fetal bovine serum (Intergen). HeLa-luc cells were stably transfected with a luciferase reporter plasmid and cultured in Dulbecco's modified Eagle medium (StemCell Technologies, Vancouver, B.C.) supplemented with 10% fetal bovine serum and 400 µg/mL Geneticin (Gibco BRL).

b. Reagents

For lipid mediated transfection studies, an expression vector, pINEX L018 in which the *Photinus pyraliste* luciferase gene (luc+ from Promegaunder the control of the CMV promoter (P. Tam, unpublished) was used. The HeLa-luc cell line was created by transfection of HeLa cells with a plasmid pINEX L032 containing the *P. pyralis* luciferase gene (Luc+ from Promega) and a neomycin resistance gene (based on pIRES1 neo from Clontech); both under the control of the CMV promoter. Supercoiled plasmid DNA was purified using a modified alkaline lysis procedure followed by purification using a CsCl/EtBr gradient (Maniatis, et al., *Molecular Cloning*, Cold Spring Harbor, N.Y. 1981, pp. 93–94).

c. Preparation of Lipoplexes

Lipoplexes were prepared as follows: All reagents were sterile and cooled to 4° C. prior to complex preparation. A solution containing 62 µM dioleoyldimethylammonium chloride:1,2-sn-dioleoylphosphatidylethanolamine (DODAC:DOPE) large unilamellar vesicles (LUVs) and a solution containing 10 µg/mL plasmid DNA were prepared in distilled water. The DNA was added to an equal volume of lipid dropwise, while vortexing. The solution was incubated on ice for 30 minutes prior to transfection. The resulting lipoplexes contained a final DNA concentration of 0.5 µg/100 µL and the cationic lipid:DNA (+:−) charge ratio was 1:1.

d. Preparation of Stable Plasmid-lipid Particles (SPLPs)

Plasmid containing a therapeutic gene was encapsulated as SPLP using the detergent dialysis method of INEX 351. The SPLP contained 42.5:42.5:15 mol % of DOPE:DODAC:1-O-[2'-(w-methoxypolyethyleneglycol)succinoyl]-2-N-octoylsphingosine, (PEG-CerC$_8$), at a lipid-:DNA ratio of 15:1 (w/w). SPLPs were separated from empty liposomes by centrifugation through a discontinuous sucrose gradient.

Figure 8A:
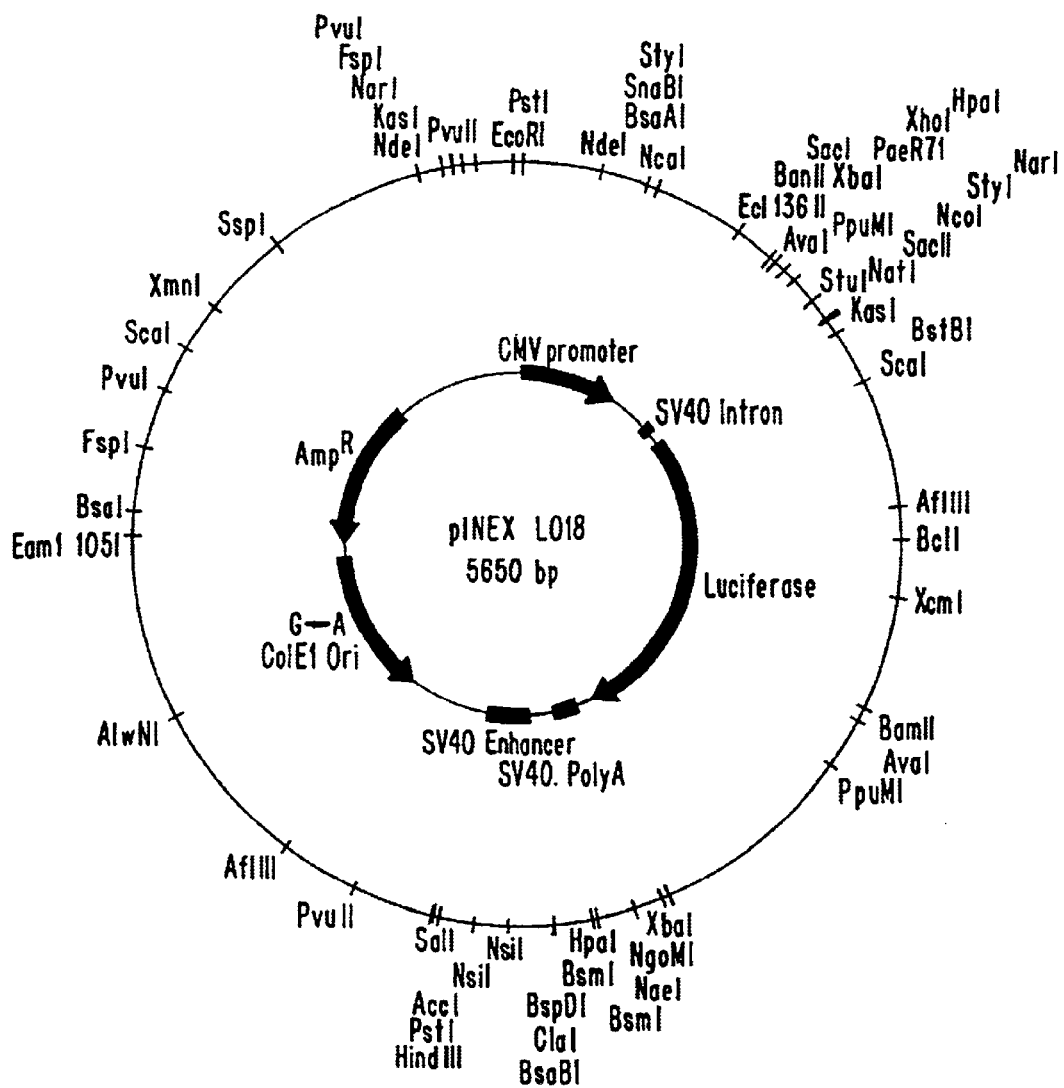
Figure 8B:
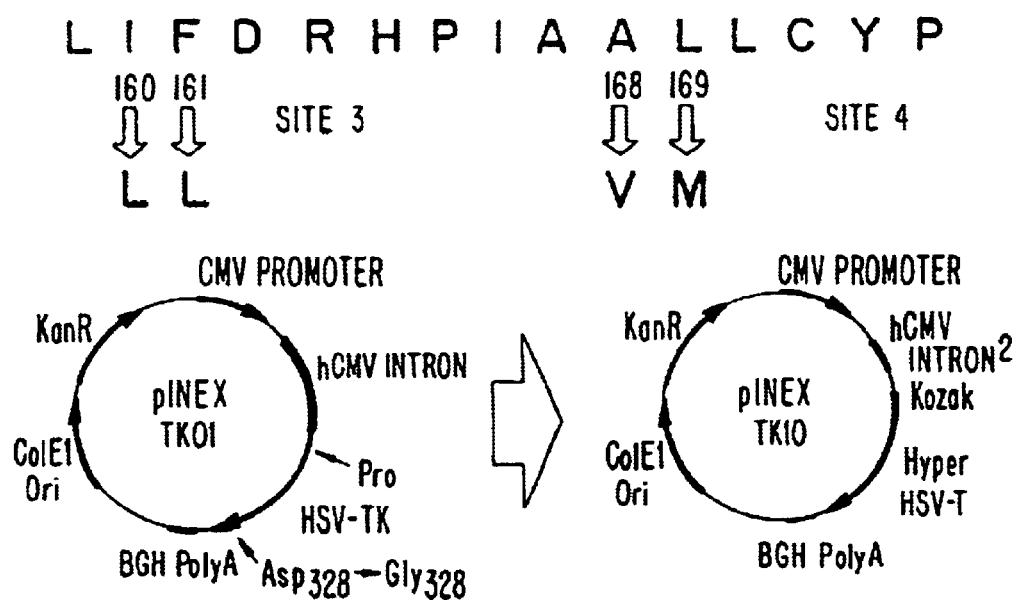
FIG. 8(B) illustrates the pINEX TK10 plasmid construct (LIFDRHPIAALLCYP= SEQ ID NO:1).

The plasmids employed in these examples are:

pINEX L018: an expression vector in which the Photinus pyralis luciferase gene (Promega, Madison Wis.) is under the control of the CMV promoter. Other genes and sequences are set out in FIG. 8A.

pINEX-TK 10: an expression vector comprising a pBR322 derived plasmid with CMV promoter linked to a "hyper" HSV-TK gene (see, Black, et al, *PNAS USA*, 93:3525–3529 (1996)). Other genes and their orientation are set out in FIG. 8B.

pINEX-IL-12: is similar to pINEX-TK10 except that the therapeutic gene comprises the IL-12 gene linked to the CMV promoter.

e. Cell Cycle Arrest and Transfection Conditions

SK-OV-3 or HeLa-luc cells were seeded at a density of 30,000 cells per well in a 24 well plate in growth media 24 hours prior to treatment with aphidicolin. Aphidicolin (Sigma) was reconstituted in phosphate buffered saline containing 0.5% DMSO. Cells were incubated with aphidicolin at a final concentration of 5 µg/mL in 1 mL of media per well for 16 hours prior to transfection. Transfection was accomplished by the addition of 0.5 µg of formulated DNA to each well.

f. Semliki Forest Virus-luciferase

Luciferase cDNA was cloned into the multiple cloning site of pSFV1-3. Recombinant virus encoding luciferase was prepared according to the protocol described by Liljestrom and Garoff (Maniatis, et al., *Molecular Cloning*, Cold Spring Harbor, N.Y., 1981, pp. 93–94). Prior to infection of SK-OV-3 cells, virus particles were activated in 0.5 mg/mL chymotrypsin for 30 minutes at room temperature. Chymotrypsin was inactivated by the addition of aprotinin to a final concentration of 0.67 mg/mL. Activated virus at a multiplicity of infection of 0.5 was added directly to the cells in growth media.

g. Assessment of Cell Cycle Status

The cell cycle status of cultures was determined by flow cytometry of permeabilized cells that were stained with propidium iodide. Prior to harvesting, media was aspirated and the cells were washed twice with 2 mL phosphate buffered saline (PBS). After washing, 2–3 drops of prewarmed trypsin-EDTA (0.25% trypsin, 1 mM EDTA; Gibco BRL) was added to each well and the plate was incubated at 37° C. until the cells had detached from the plate. Trypsin was inactivated by the addition of 1.5 mL of cold media. The samples were transferred to 6 mL polystyrene tubes (Becton-Dickenson, San lose, Calif., USA) and centrifuged at 2000 rpm for 5 min (Beckman GS-6 R, rotor GH3.8). Cells were fixed and permeabilized by incubation for 10 min in 70% methanol (pre-chilled to −70° C.). Samples were then centrifuged at 2000 rpm for 5 min and the cells were incubated in 0.5 mL of 150 μg/mL propidium iodide (Molecular Probes, Eugene, Oreg.) in PBS for 30 minutes on ice in the dark prior to analysis by flow cytometry. 5,000 cells were analyzed in the FL2 channel ($\lambda_{emission}$=585+/−21 nm) of a FACSort flow cytometer (Becton-Dickinson, San Jose, Calif.) equipped with an Ar- ion laser ($\lambda_{excitation}$=488 nm)

For the plasmid DNA uptake experiments, the method previously described (Zabner, et al., *J. Biol. Chem.*, 270:18997–19007 (1995); Tseng, et al., *Biotechnol. Bioeng.*, 50:548–554 (1996)) using fluorescentiy labeled DNA and flow cytometry was used with the following modifications. Plasmid DNA was fluorescently labeled by incubation with YOYO-1 iodide (Molecular Probes, Eugene, Oreg.) at a dye:basepair ratio of 100:1 for 10 minutes at 4° C. The sample was then dialyzed twice against autoclaved deionized water.

Lipoplexes were prepared using YOYO-1 labeled DNA and incubated with cells. The cells were washed 3x with PBS and detached from the wells by trypsin as described above. The cells were washed 3x in PBS prior to analysis by flow cytometry. Fluorescence was measured in the FL1 channel ($\lambda_{emission}$=530+/−15 nm) of a FACSort flow cytometer (Becton-Dickinson, San Jose, Calif.) equipped with an Ar- ion laser ($\lambda_{emission}$=488 nm). Data was collected from 10,000 cells and analyzed for fluorescence using CellQuest software. Analysis by microscopy showed that most of the fluorescence associated with the cells was intracellular and associated with subcellular organelles.

h. Luciferase and Protein Assays

Luciferase assays were performed using the Luciferase Assay System kit (Promega, Madison, Wis.) according to the manufacturer's protocol. Cell samples were washed twice with PBS, lysed by incubation with 200 μL of lysis buffer (0.1% triton in 250 mM $NaH_2PO_4$, pH 7.4) for 20 min. 20 μL of cell lysate was assayed (in duplicate) using a mL3000 microtiter plate luminometer (Dynex Technologies). A standard curve was determined by assaying 20 μL of serial dilutions of a 1 mg/mL luciferase standard (Boehringer Mannheim). Cell lysate was assayed for protein content using the bicinchoninic acid (BCA) colorimetric method. Briefly, in a 96 well plate, 95 μL of water and 100 μL of the Micro BCA protein assay working reagent (Pierce) were added to 5 μL of cell lysate. The plates were shaken on a rotary platform at 100 rpm for 10 minutes before being incubated at 37° C. for 2 hours. Absorbance was monitored at 570 nm (Dynatech MR5000 plate reader) and protein content calculated using a standard curve of varying concentrations of BSA.

4. Cell Cycle Arrest by Treatment with Aphidicolin

Aphidicolin inhibits DNA polymerase α and δ, the two major polymerases involved in DNA synthesis during the S-phase (see, Ikegami, et al., *Nature*, 275:458–460 (1978); Wahl, et al., *Biochemistry*, 25:7821–7827 (1986); Legendre, et al., *Pharm. Res.*, 9:1235–1242 (1992)), and specifically arrests cells in the $G_1/S$ boundary.

In an initial study, the effectiveness of a non-lethal concentration of aphidicholin to arrest SK-OV-3 cells was determined. A sub-confluent asynchronous cell culture contained approx. 75%, 5% and 20% of cells in $G_1$, S and M phase, respectively, as measured by staining with propidium iodide (PI) followed by flow cytometry (FIG. 1(A)). Treatment of cell cultures with aphidicolin at a final concentration of 5 μg/mL for 16 hrs causes effective arrest resulting in >95% of the cells in $G_1$ phase of the cell cycle (FIG. 1(B)). All subsequent experiments utilized these conditions for cell cycle arrest.

Figure 2:
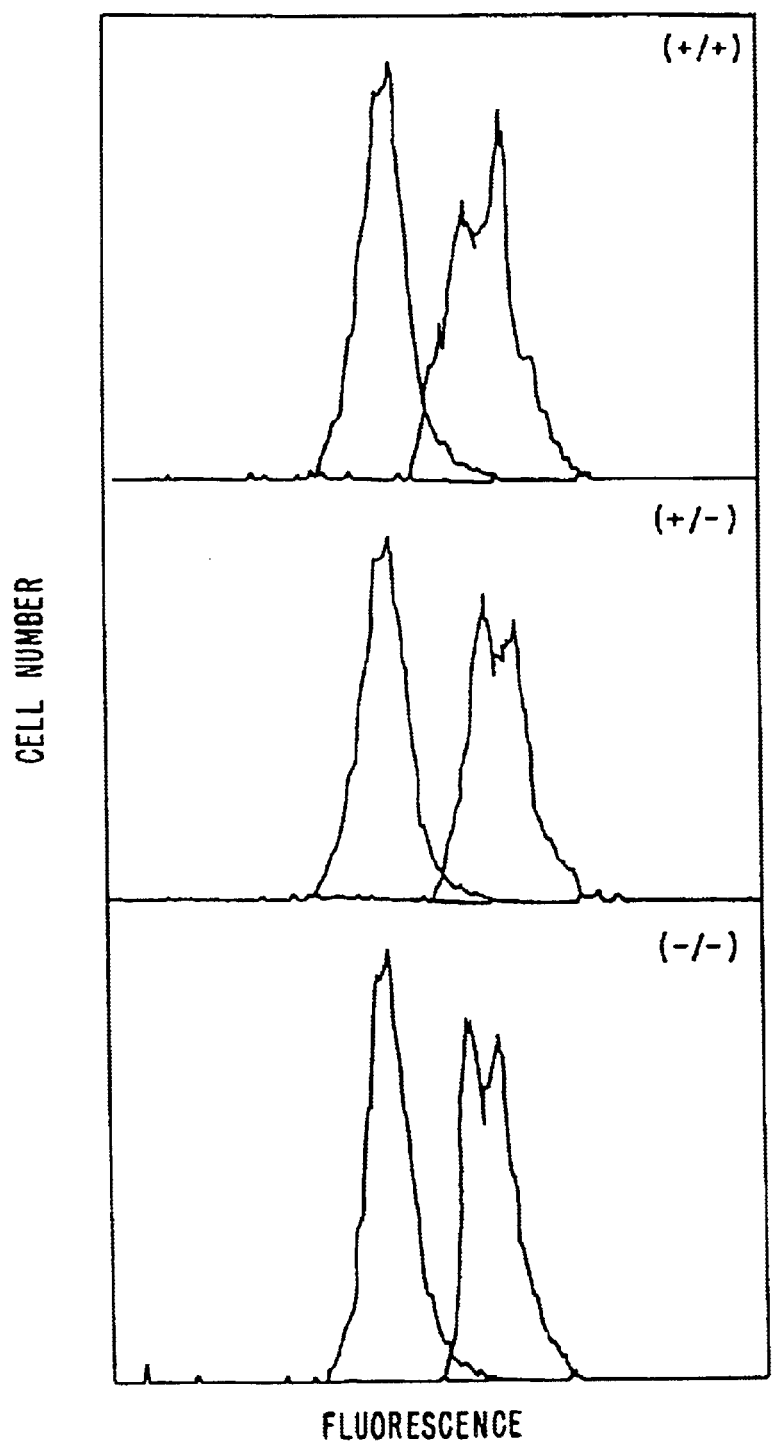
FIG. 2: DNA uptake in SK-OV-3 cells. Shown are histograms of relative YOYO-1 iodide/DNA fluorescence versus number of cell obtained by flow cytometry. Plasmid DNA was labeled with YOYO-1 iodide and formulated as lipoplexes. After a 16 hr incubation with aphidicolin to arrest cells in the $G_1$ phase of the cell cycle, cultures were incubated with DODAC:DOPE:plasmid lipoplexes for 1 hr in the continuous presence of aphidicolin (+/+) or in the absence of aphidicolin to remove the cell cycle arrest (+/−). An asynchronous culture that had never been exposed to aphidicolin (−/−) was used as a control. Cells were harvested as described in the Example Section at the time points indicated and analyzed by flow cytometry. The histogram on the left of each panel is the fluorescence profile of cells incubated with naked YOYO-1 labeled plasmid DNA and represents a negative control. The relative increase in fluorescence, relative to naked DNA, indicates internalization of the lipoplexes.

In order to determine whether aphidicolin treatment affects cellular processes related to transgene expression, effects on DNA uptake and gene expression were studied. It has been shown previously that fluorescently labeled DNA can be formulated as lipoplexes and the uptake of lipoplexes can be measured by flow cytometry (see, Zabner, et al., *J. Biol. Chem.*, 270:18997–19007 (1995); and Tseng, et al., *Biotechnol. Bioeng.*, 50:548–554 (1996); Tseng, et al., *Biotechnol. Bioeng.*, 50:548–554 (1996)). Cells arrested with aphidicolin were incubated with lipoplexes containing plasmid DNA labeled with the fluorescent dye YOYO-1 in the absence (+/−) or continued presence of aphidicolin (+/+) and compared to control asynchronous cells that had never been exposed to aphidicolin (−/−). The rate of lipoplex uptake per cell was determined by flow cytometry. FIG. 2 shows that the lipoplexes were efficiently internalized in all cultures with greater than 90% of the cells exhibiting fluorescence by the end of the first hour of incubation. The level of fluorescence within the cells reached a maximum within one hour and was maintained up to four hours (not shown). Thus, the rate of accumulation of fluorescence within cells arrested with aphidicolin was comparable to control cells which had not been exposed to aphidicolin. These results demonstrate that cell cycle arrest by aphidicolin treatment does not affect the internalization of lipoplexes by SK-OV-3 cells.

Figure 3:
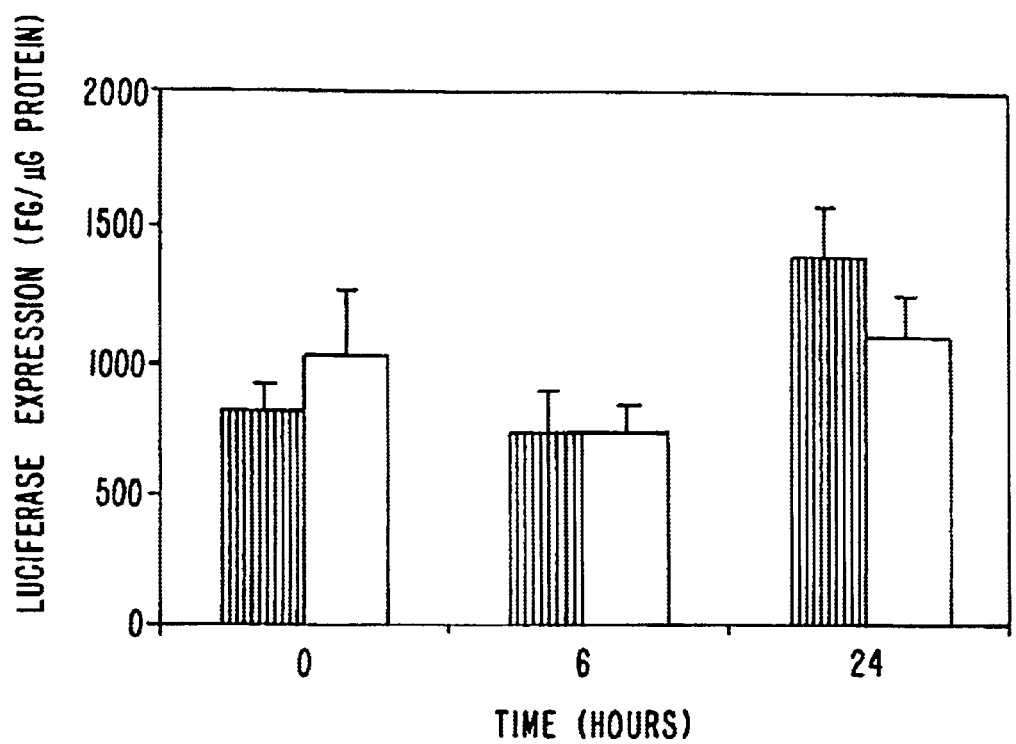
FIG. 3: Effect of aphidicolin on gene expression in HeLa-luc cells. HeLa-luc cells were arrested in the $G_1$ phase of the cell cycle by the administration of aphidicolin as described in the Example Section. Luciferase gene expression was measured at 0, 6 and 24 hours after arrest for both untreated cells (open bars) and cells blocked in the $G_1$ (solid bars) phase of the cell cycle.

To determine the effect of aphidicolin-mediated cell cycle arrest on the transcriptional and translational machinery of the cell, a clonal HeLa cell line stably transfected with a CMV driven luciferase expression cassette (Song, Inex Pharmaceuticals, unpublished) was analyzed. This cell line, HeLa-luc, was engineered to constitutively express the gene encoding luciferase. If aphidicholin treatment down regulates CMV driven transcription or the host cells ability to transport and translate the luciferase mRNA, it is expected that aphidicholin treated HeLa-luc cells would contain less luciferase activity than untreated cells. FIG. 3 shows that treatment with aphidicolin did not significantly affect the level of luciferase gene expression when compared with the untreated control cells.

The results from these experiments illustrate that aphidicolin treatment effectively arrests cells in $G_1$ phase of the cell cycle with negligible concomitant effects on the internalization of lipoplexes and processes involved in gene expression.

Figure 4:
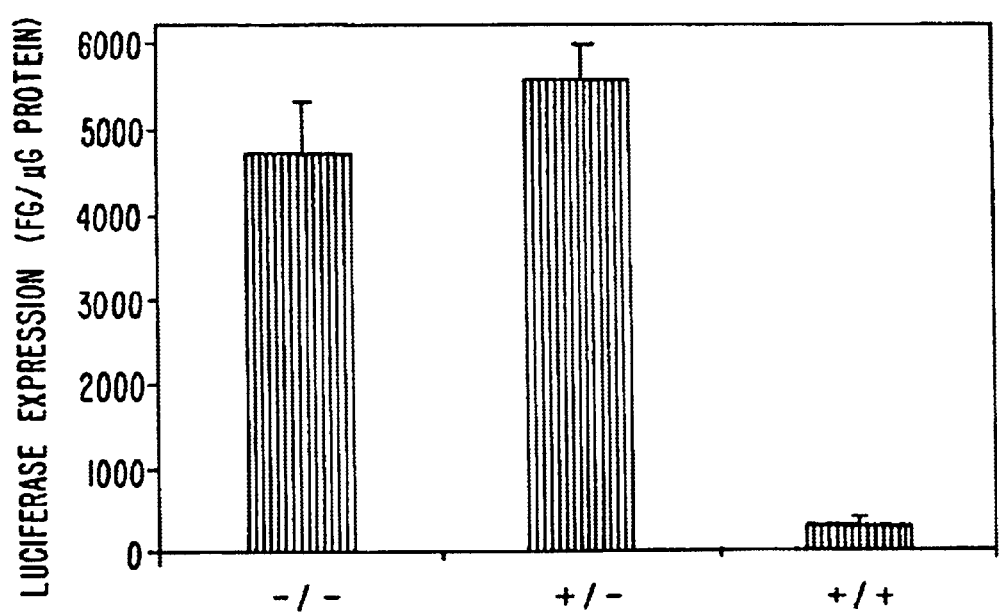
FIG. 4: Effect of cell cycle arrest on lipoplex mediated transfection. Cells were arrested in the $G_1$ phase of the cell cycle by treatment with aphidicolin, incubated with 0.5 µg plasmid containing lipoplexes that encoded luciferase, and assayed for luciferase activity. (−/−) represents control cultures that have never been exposed to aphidicolin; (+/−) represents cultures that were synchronized with treatment with aphidicolin, but then incubated with lipoplexes in the absence of aphidicolin; (+/+) represents cultures that were synchronized with treatment with aphidicolin and were then incubated with lipoplexes in the continued presence of aphidicolin. Luciferase activity was measured after 24 hours of incubation with lipoplexes. The data is presented as the mean of triplicate samples±s.d.

5. Cells Arrested in the $G_1/S$ Phase by Aphidicolin are not Transfected Efficiently by Lipoplexes An initial experiment was performed to determine whether lipid mediated transfection was affected by the cell cycle status of SK-OV-3 cells in vitro. Cell cultures were synchronized in the $G_1$ phase of the cell cycle by aphidicolin treatment and incubated with DODAC:DOPE lipid/DNA lipoplexes either in the presence of aphidicolin to continue the cell cycle arrest (+/+), or in the absence of aphidicolin to remove cells from cell cycle arrest (+/−). Luciferase activity was measured after 24 hrs of continuous exposure to lipoplexes. FIG. 4 shows that luciferase expression from (+/−) cultures did not differ significantly from control asynchronous cell culture that had never been exposed to aphidicolin (−/−). In comparison, the synchronous (+/+) culture arrested in the $G_1$ phase demonstrated a 20-fold decrease in luciferase gene expression. Cell cycle analysis of the synchronous (+/+) culture revealed that approximately 95% of the cells remained arrested in the $G_1$ phase at the end of the 24 incubation with lipoplexes (not shown). The cell cycle status profile of the (−/−) culture from which the cell arrest had been removed approximated the profile of the control (−/−) culture (not shown). These results suggest that aphidicolin treatment and the concomitant cell cycle arrest inhibits cationic lipid mediated transfection at a certain, as yet unidentified, point during the transfection process.

6. Kinetics of Lipid Radiated Transfection in Aphidicolin Treated Cells

Figure 5:
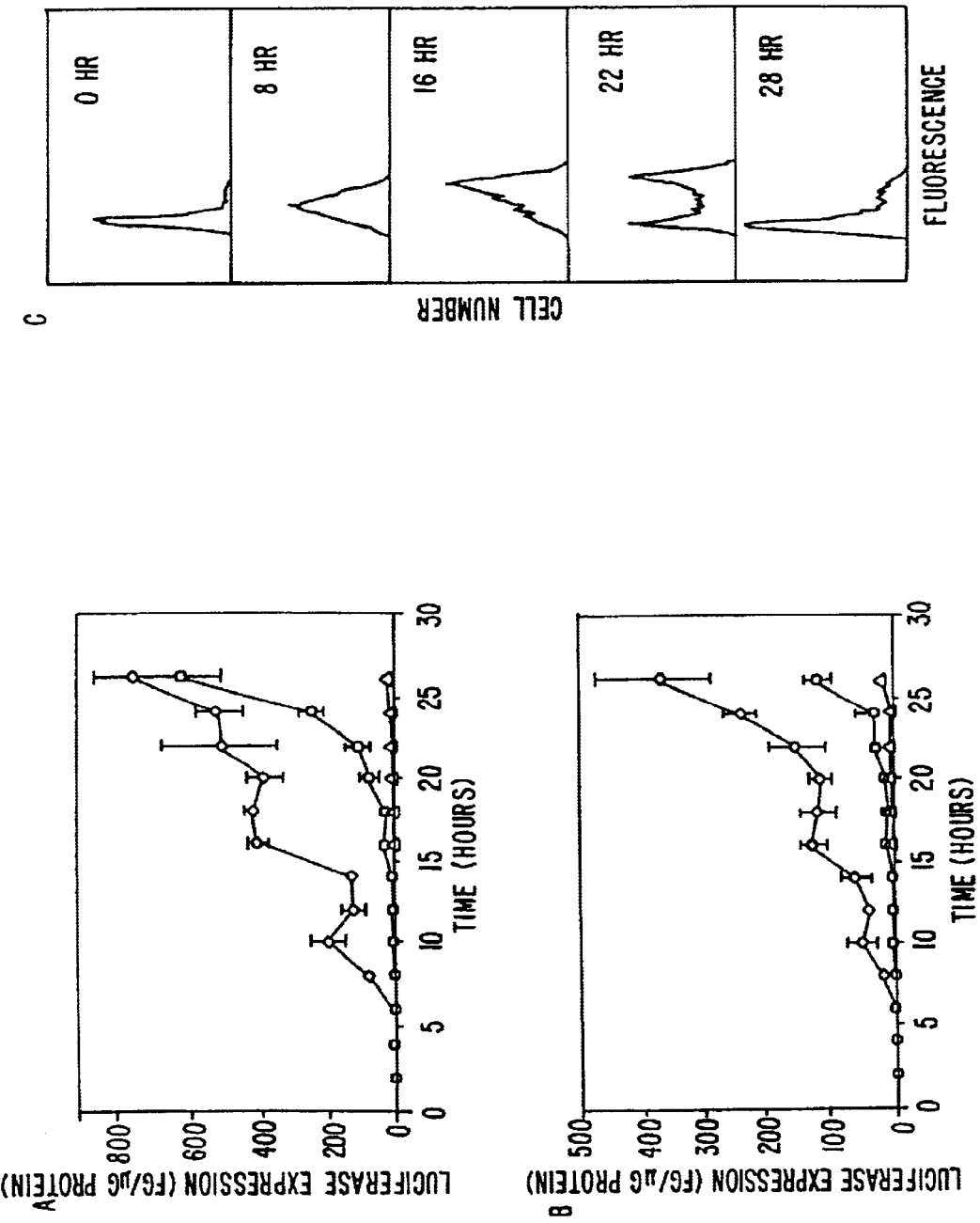
FIG. 5: Correlation of kinetics of luciferase gene expression in aphidicolin treated cells allowed to progress through the cell cycle. SK-OV-3 cells were arrested as described in the Example Section. At time (t=0), cells synchronized with aphidicolin were incubated with 0.5 µg of plasmid DNA formulated as either lipoplexes (A) or SPLPs (B) in the absence (+/−) (■) or continued presence (+/+) (▼) of aphidicolin. Asynchronous cultures that had never been exposed to aphidicolin (−/−) (♦) were used as controls. Samples were harvested at 2 hr intervals and analyzed for luciferase activity as well as cell cycle status (C). Analysis of cell cycle status was determined at the time points shown as described in the Example Section. Luciferase expression is expressed as the mean of triplicate samples±s.d.

In order to gain a further understanding of lipid-mediated transfection processes in proliferating and non-proliferating cells, we measured and correlated the kinetics of cell cycle status and luciferase gene expression from (+/+), (+/−) and (−/−) cultures after continuous incubation with either lipoplexes or SPLPs were measured and correlated Cell cycle status and luciferase activity of each culture were determined at 2 hr intervals after the initiation of incubations (t=0) with the lipoplexes. FIG. 5 shows the correlation of cell cycle status of a (+/−) culture and the kinetics of luciferase gene expression after incubation with either lipoplexes (FIG. 5(A)) or SPLPs (FIG. 5(B)). Incubation with either lipid formulations in (+/+) cultures show extremely low levels of luciferase activity throughout the course of the experiment. In the (+/+) cultures, 95% of the cells remained arrested in the $G_1$ phase throughout the course of the experiments (not shown). The (−/−) cultures began to exhibit significant luciferase activity after 6–8 of incubation with either lipid formulation. The levels of luciferase activity progressively increased and reached maximal levels at 26 hrs when the experiment was terminated. At this time, an approximately 40-fold difference in luciferase activity was observed between (−/−) and (+/+) cultures treated with lipoplexes and a 20-fold difference when treated with SPLPs. The cell cycle profile of the (−/−) cultures remained unchanged and characteristic of a proliferating asynchronous culture throughout the course of the experiment (not shown). Incubation of the (+/−) culture with both formulations resulted in a delayed onset of luciferase expression compared to the control (−/−) culture; exposure to lipoplexes resulted in significant luciferase expression only after 16 hrs. Exposure to SPLPs resulted in luciferase expression even later, at 20–22 hrs. Analysis of the cell cycle status revealed that within 6–8 hours after the removal of the aphidicolin block in (+/−) cultures, cells had resumed their progression through the cell cycle and had accumulated in the S phase (FIG. 5(C), 8 hr), By 16 hrs, approximately 85% of the cells in the (+/−) culture had progressed through the S phase and were in the $G_2$/M phase (FIG. 5(C), 16 hr). Within 22 hrs, close to 45% of the cells had undergone mitotic division and had progressed into the $G_1$ phase (FIG. 5(C), 22 hr). Thus, higher luciferase activity in cultures incubated with either lipid formulations appeared to coincide with the passage of cells into the $G_2$/M phase and the $G_1$ phase of the subsequent cell cycle. Continued exposure of the (+/−) cultures with either lipid formulations resulted in a progressive increase in luciferase levels and a concomitant increase in the number of cells in the $G_1$ phase (FIG. 5(C), 26 hr). This increase corresponds to an accumulation of cells that have undergone a mitotic division. In (+/−) cultures incubated with either formulation, the increase in luciferase activity appeared to occur in two phases. In cells incubated with lipoplexes, the first phase occurred between 16–22 hours and represents a slower rate of increase in luciferase expression than the second phase which occurred between 22–26 his (FIG. 5(a) In cells incubated with SPLPs, the first phase occurred between 20–24 hrs and a second phase representing a faster rate of increase in luciferase expression occurred between 24–26 his (FIG. 5(b)). In (+/−) cultures incubated with either formulation, the second phase corresponds to an increased number of cells in the $G_1$ phase due to an increased number of cells that had undergone mitotic division. Therefore, these experiments demonstrated that increase in luciferase expression in (+/−) cultures paralleled the increase in the number of cells undergoing mitotic division.

Figure 6:
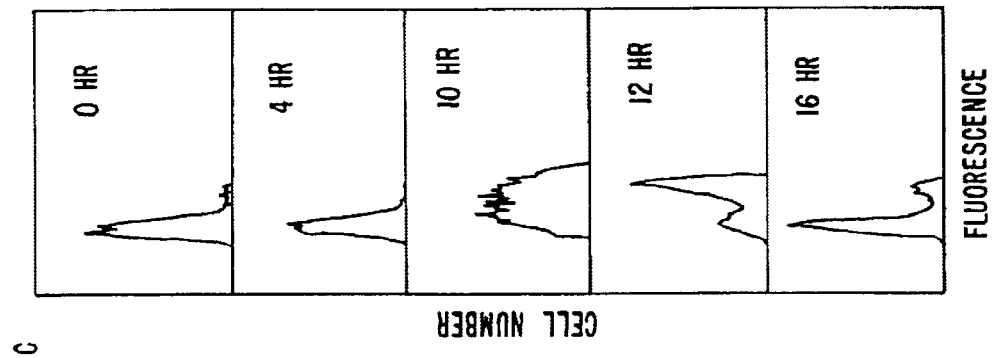
FIG. 6: Determination of the period most amenable to transfection in aphidicolin treated cells allowed to progress through the cell cycle. Cultures that had been synchronized by the treatment with aphidicolin were allowed to proceed through the cell cycle by replacing the media with aphidicolin free media (at t=0) (■) and compared for luciferase gene expression with asynchronous cells that had never been exposed to aphidicolin (♦). At 2 hrs intervals (T=2, 4, 6, etc), the cultures were incubated with 0.5 µg plasmid DNA formulated as either (A) lipoplexes or (B) SPLPs in the absence of aphidicolin. The cultures were analyzed for their cell cycle status at the time of incubation with the formulated DNA (C). After 1 hr of incubation, the formulations were removed and the cells were cultured for a further 5 hrs in the absence of formulation and aphidicolin and analyzed for luciferase activity. Luciferase expression is expressed as the mean of triplicate samples±s.d.
Figure 6:
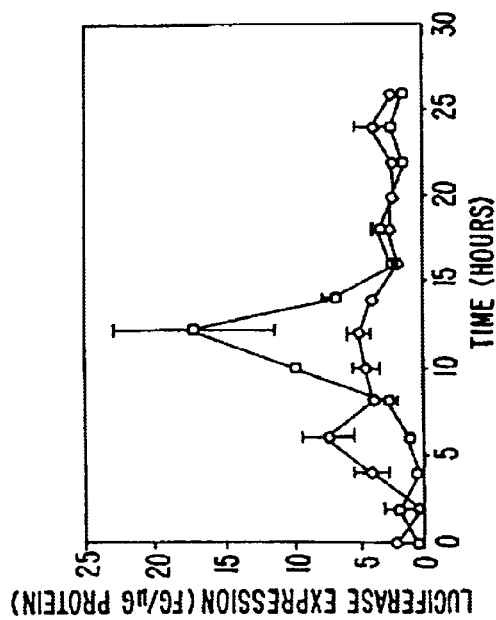
Figure 6:
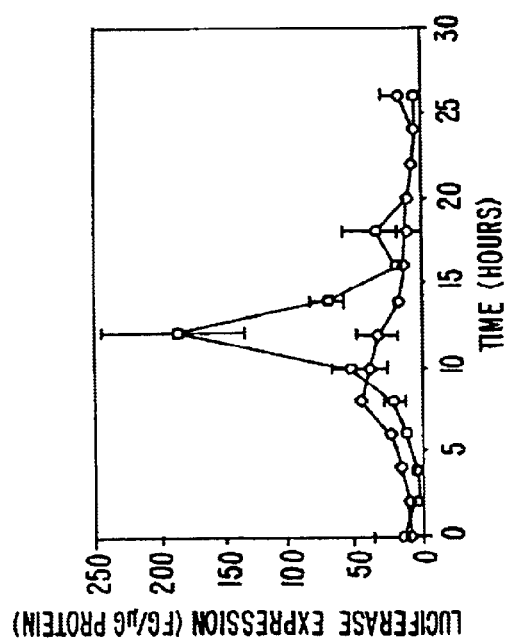

In order to ascertain the relationship between mitotic division and lipid mediated transfection, a variation of the experiment described above was performed. Cells synchronized in the $G_1$ phase by aphidicolin were released from cell cycle arrest by washing the cells with PBS and replenishing the cells with fresh aphidicolin-free media (t=0). At 2 hr intervals thereafter (i.e., t=2 or 4 or 6, etc), these (+/−) cultures were exposed to lipoplexes or SPLPs for one hour after which the media was removed and the incubation continued for a further 5 hr in aphidicolin-free and formulation-free media for a further 5 hours. The cells were then harvested and analyzed for luciferase activity. An asynchronous culture (−/−) that had never been exposed to aphidicolin was transfected and analyzed in parallel. FIGS. 6(A) and (B) show the transfection profiles of cultures incubated with lipoplexes or SPLPs, respectively. With either formulation, luciferase expression was observed to increase in (+/−) cultures, beginning at approximately 10 hours after the removal of aphidicolin and reaching a maximum at 12 hours. When compared to the (−/−) control culture, the (+/−) cultures exhibited 3-fold and 8-fold increases in luciferase expression with lipoplexes and SPLPs, respectively. Analysis of the cell cycle status of the (+/−) cultures indicated that progression of cells from $G_2$/M phase into $G_1$ phase had occurred at 10 hours after the removal of aphidicolin (FIG. 6(C), 10 hrs). The peak in luciferase expression at 12 hours coincided with the highest number of cells transiting from the $G_2$/M into $G_1$ phase corresponding to the highest number of cells having undergone mitosis (FIG. 6(C), 12 hrs). After this time, the luciferase activities subsided and by 16 hours had reverted to levels comparable to those in the control cultures. This decline in luciferase activity coincides with the reduction in the number of mitotic cells entering $G_1$ phase.

These results indicate that luciferase gene expression in cultures exposed to cationic lipid transfection systems was dependent on the number of cells undergoing mitotic cell division. A one-hour exposure to lipid formulated plasmid DNA was sufficient to elicit detectable luciferase gene expression if it coincided with cells undergoing mitotic division.

Figure 7:
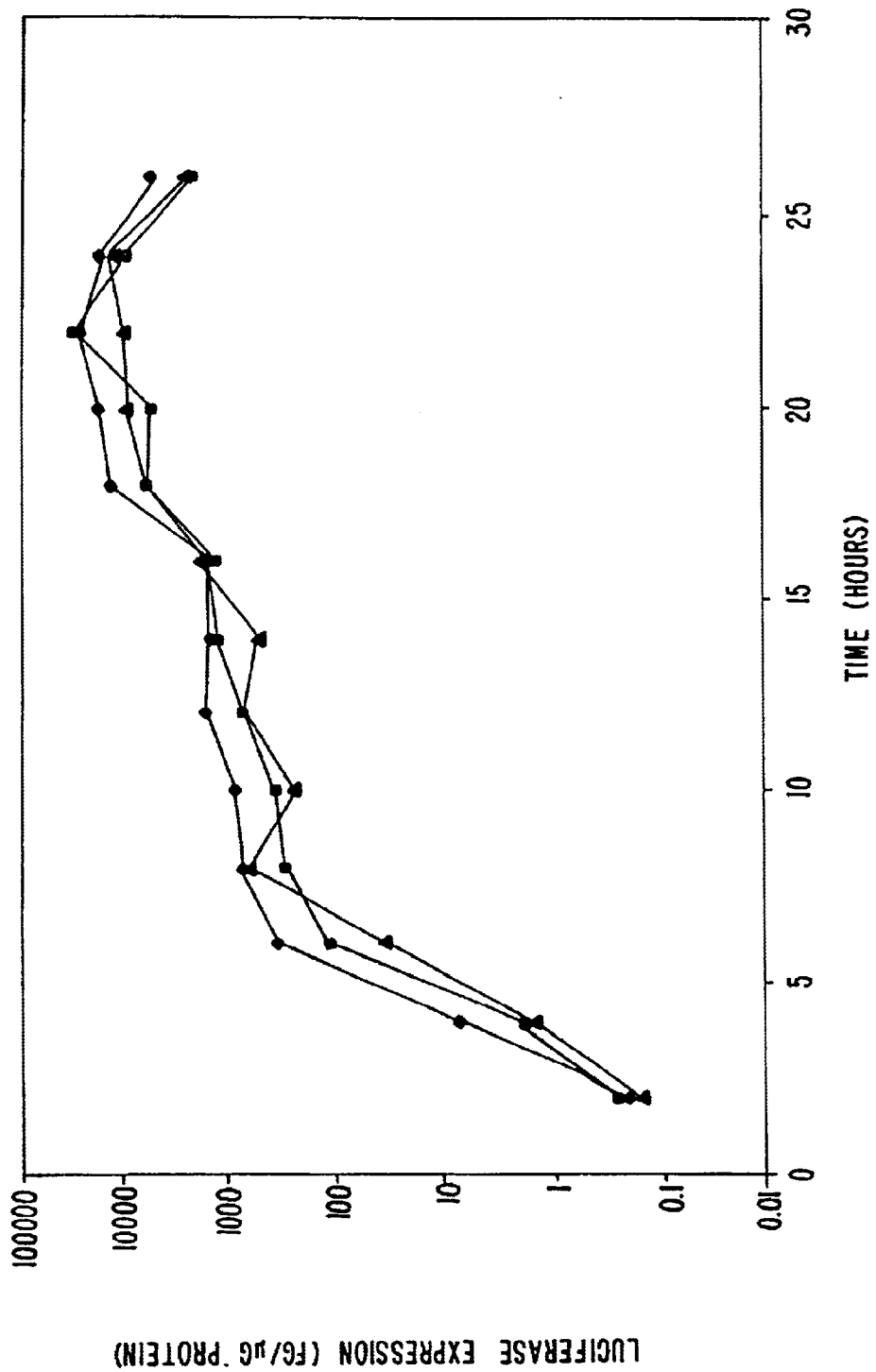
FIG. 7: Semliki Forest Virus Mediated Gene Expression. SK-OV-3 cells were arrested as described in the Example Section. At time 0, arrested cells were released from the cell cycle block by the addition of fresh media without aphidicolin; blocked cells were supplemented with aphidicolin in fresh growth media. At this time, all cells were infected with SFV-luc at a multiplicity of infection of 0.5 as described in the Example Section. Gene expression (luciferase) was measured every two hours for untreated cells (♦), cells released from the aphidicolin block (■) and cells that were arrested throughout the experiment (▼). Luciferase expression is expressed as the mean of triplicate samples.

7 The Effects of Aphidicolin Arrest on Semliki Forest Virus Mediated Gene Expression In order to determine if transfection systems that do not require nuclear delivery of the exogenous nucleic acids are dependent on cell division, the relationship between transfection and cell proliferation in the alphavirus Semliki Forest Virus (SFV) was investigated. Alphaviruses are enveloped viruses that contain a positive sense strand RNA genome. The genomic RNA serves as a substrate for cytoplasmic translation and replication upon infection. Infection with replication defective SFV vectors is therefore not dependent on nuclear delivery of the genetic material. The virus, SFV-luc, used in this study contained the gene encoding luciferase in place of the viral structural genes. SK-OV-3 cells were arrested in $G_1$ prior to infection with SFV-luc (m.o.i.=0.5) as described above. The kinetics of luciferase gene expression were determined and compared with (−/−), (+/−) and (+/+) cultures. There was no significant difference in the pattern of gene expression between the three types of cell cultures tested (FIG. 7). This observation suggests that transfection systems that do not require entry into the nucleus function independently of the cell cycle. The results from this experiment also support the earlier observation (see, FIGS. 2 and 3) that aphidicolin-mediated cell cycle arrest does not effect internalization by endocytotic pathways and cellular gene expression machinery.

The following in vivo examples employ OncoTCS, which comprises vincristine sulfate encapsulated in sphingomyelin/cholesterol (SM/chol=55:45 by mol %) liposomes, prepared according to the methods disclosed in U.S. Pat. Nos. 5,543,152 and 5,741,516, the teachings of which are incorporated herein by reference. The known therapeutic dosage of liposomal vincristine is 2 mg/kg. Doses below this level are considered subtherapeutic. A 200 μL dosage of OncoTCS administered to an approximately 25 g mouse is approximately 0.5 mg/kg vincristine sulfate and 10 mg/kg lipid. These liposomes provide extended release of vincristine. Vincristine sulfate in the free form may also be used in the methods of the present invention.

8. Effect on In vivo Transformation Efficiency

25 C57 mice are seeded intraperitoneally with about 100,000 B16 cells. On day 7, 12 mice are injected i.v. via the tail vein with about 0.5 mg/kg of OncoTCS (vincristine sulfate encapsulated in sphingomyelin-containing TCS) in about 200 microliters. 12 control mice are not treated with OncoTCS. 24 hours later, all mice are injected i.p. with 20 micrograms of INEX 324 (TCS containing luciferase plasmid pINEX L018) in 500 microliters. Tumors are harvested 6, 12, 24 and 48 hours later, fast frozen, and stored at −70° C. until analyzed for luciferase activity. The frozen organs are then thawed at room temperature. 600 microliters of 1× cell culture lysis buffer (Promega) is added and the samples are homogenized in a FASTPREP homogenizer for 20 sec. at speed 4.0. The samples are centifuged for 2 min. at 10,000 g, and 20 microliters of the supernatant is assayed for luciferase activity. The results demonstrate transfection of neoplastic sites following treatment with vincristine.

9. In vivo Synchronization of Cells at a Tumor Site by Administration of a Cell This example demonstrates the synchronization effect caused by the cell cycle blocker vincristine at a tumor site.

Mice carrying MCA 207 tumors (prepared as described in other examples) were injected at time 0 i.v. via tail vein with either empty OncoTCS (i.e., empty SM/chol liposomes; 10 mg/kg lipids in 200 μL total solution) or OncoTCS (200 μL dosage: 0.5 mg/kg vincristine sulfate).

Mice were euthanized either at 24 h or at 72 h after treatment. Tumors were excised and evaluated as follows. Freshly harvested tumors were homogenized in 7 mL of media into single cells using a Dounce homogenizer (10–15 strokes). The cell suspension was carefully decanted into a 15 ml. Falcon tube ensuring that non-homogenized tissue was not collected. The cells were centrifuged for 5 min at 1000 g (4° C.). The cell pellet was thoroughly resuspended in 2 mL 70% methanol and stored at 70° C. for 20 min. The cells were then pelleted by centrifugation for 5 min at 1000 g (4° C.). The cell pellet was resuspended in 1 mL 100 μg/mL propidium iodide and stored at 4° C. for 15 min before analysis by flow cytometry. Flow cytometry analysis was performed on FACSort (Becton-Dickinson) and cells analyzed on FL2 channel utilizing doublet discrimination mode.

Figure 9:
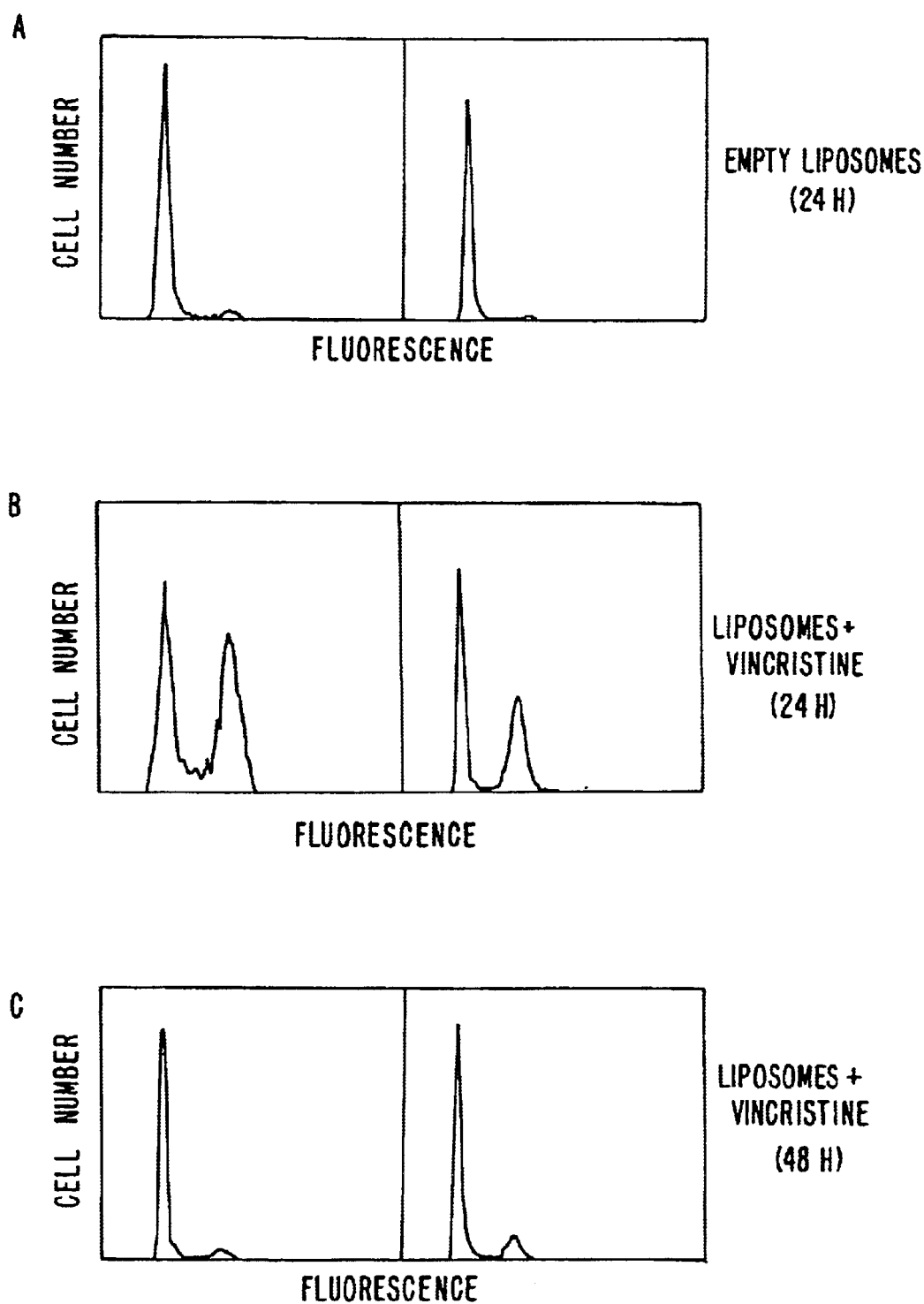
FIG. 9: Cell cycle status of cells at tumor site (MCA 207) in response to treatment with vincristine. n=normal chromosome complement. Empty SM/Chol liposomes (control) (FIG. 9(A)); 24 h after treatment with OncoTCS (FIG. 9(B)); and 48 h after treatment with OncoTCS liposome+ vincristine) (FIG. 9(C)).

Data in FIG. 9 is presented as a histogram showing FL2-Area (x-axis) vs. number of cells (y-axis). n=normal somatic cell DNA content; 2n=cells accumulated at phase immediately prior to cell division. FIG. 9A demonstrates that mice MCA 207 tumors treated with empty OncoTCS cells evidence very few cells (<5%) at the 2 n phase after 24 h, essentially the same as the negative control. Cell cycle distribution is approximately 85%, 5% and 10% in G0/G1, S and G2/M phases, respectively. FIG. 9B demonstrates a significant accumulation at 24 h after OncoTCS administration of tumor cells at the 2 n phase (45–55%, 5–10% and 35–45% of cells in G0/G1, S and G2/M phases of the cell cycle, respectively). Thus, the number of cells in G2/M phase increased by 3 to 4.5 fold upon treatment with OncoTCS. FIG. 9C demonstrates that by 48 h after vincristine treatment, most cells have progressed through the cell cycle block and are returning to their normal pretreatment distribution. The results demonstrate that a subtherapeutic amount of vincristine results in effective transient synchronization of cells at the 2 n phase, with a significant accumulation at 24 h. The results suggest that accumulation of the therapeutic nucleic acid at the tumor site in the period around 24 h–48 h after OncoTCS administration would provide the greatest therapeutic advantage.

10. Improved In vivo Transfection of Reporter Gene Following Treatment with a Cell Cycle Blocking Agent a. Direct injection of DNA into tumors of MCA 207 and U87 Tumor Bearing Mice This example demonstrates that pretreatment of mice bearing subcutaneous tumors with the vines alkaloid drug vincristine improves transfection at the tumor site of a reporter gene construct pINEX L018 encapsulated in an INEX 351 lipid formulation administered by direct intratumoral injection. This example uses mice bearing MCA 207 fibrosarcoma tumor cells (provided by S. Rosenberg, National Cancer Institute, Frederick/Bethesda, Md.), but the data suggests that any standard tumor model, including Lewis Lung or U87 tumors will respond to the methods of the present invention.

C57 BL/6 mice are seeded subcutaneously with MCA 207 tumor cells. Tumor seeding is performed by standard techniques. Mice were seeded subcutaneously on the hip flank with 100,000 MCA-207 fibrosarcoma tumor cells by subcutaneous injection on day zero. The tumor cells had been cultivated and prepared according to standard techniques using RPM media with 10% Fetal Bovine Serum (see, for example, *Current Protocols in Molecular Biology*, Eds. Ausubel, F. M., et al.)

On day 7–10, when tumors had developed to useable sizes, mice were injected i.v. via tail vein with approximately 0.5 mg/kg of OncoTCS (200 μL) (subtherapeutic amount of vincristine). Vincristine sulfate in the free form may also be used in known therapeutic dosages. Control mice were injected with empty SM/chol liposomes. 20–24 hr later, all mice are injected intra-tumorally with 2 μg DNA reporter gene construct pINEX L018 of INEX 351 (approximate lipid dose=10 μg; total volume 20 μL). At various time points after 351 injections (as identified in the results), tumors are harvested and fast frozen and stored at −70° C. until analyzed for luciferase activity.

Luciferase assay: The frozen tissues are thawed to room temperature. 600–800 μL of 1× cell culture lysis buffer (Promega) is added and the samples are homogenized in the FASTPREP homogenizer for 20 sec at speed 4.0. The samples are centrifuged for 2 min at 10,000 g and 20 μL of the supernatant is assayed for luciferase using standard techniques.

Figure 10:
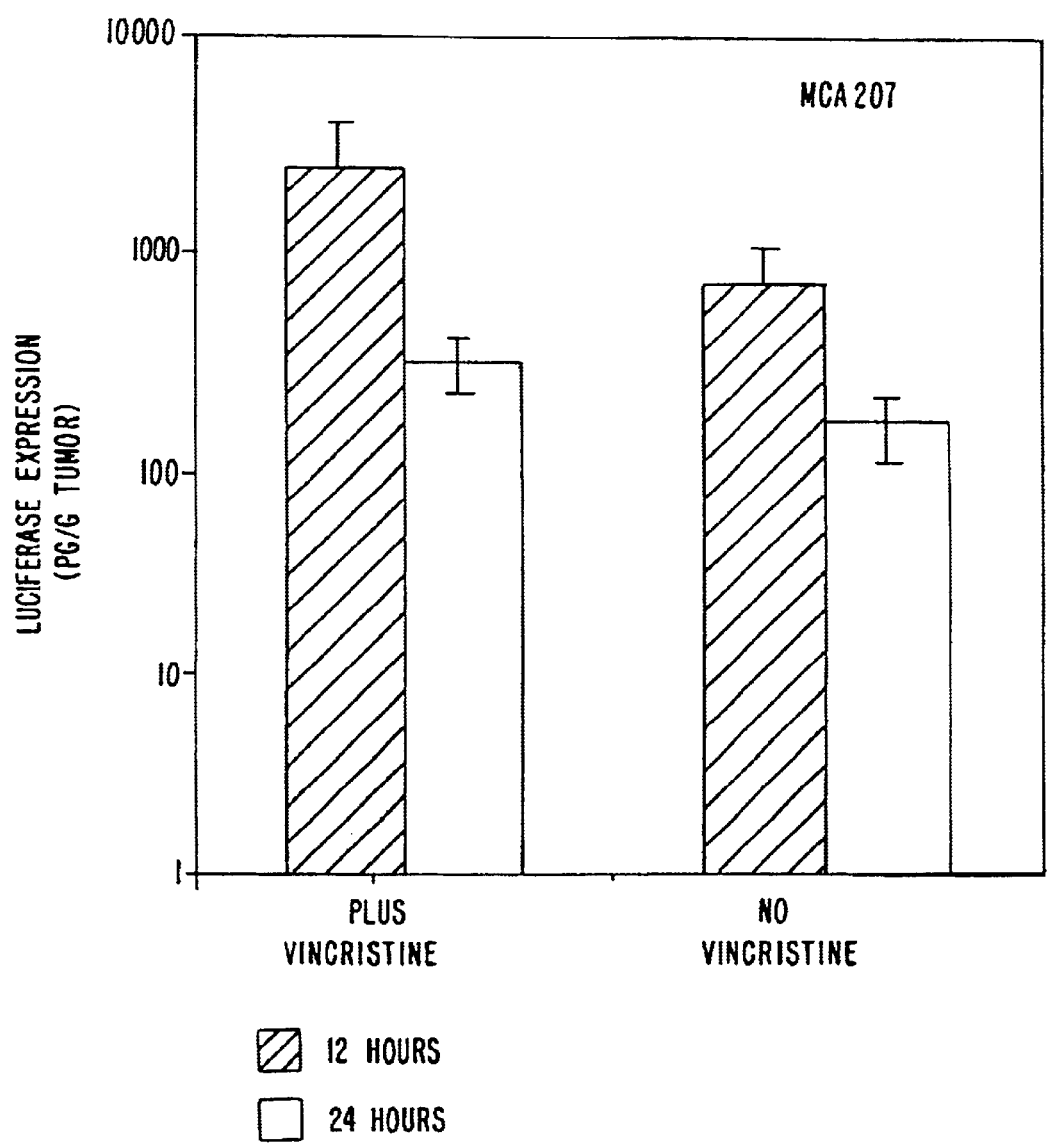
FIG. 10: Effect of Pretreatment of OncoTCS (i.v. 0.5 mg/kg) on transfection of MCA 207 tumors using INEX TCS 351 (i.t. 2 µg) (Tumors harvested after 12 h).

FIG. 10 demonstrates the effect of pretreatment of OncoTCS (i.v., 0.5 mg/kg) on transfection and expression of pINEX L018 at an MCA 207 tumor site using an INEX 351 formulation (i.t., 2 μg DNA). Tumors were harvested either 12 h or 24 h after administration of the plasmid. Luciferase activity calibrated per gram of tumor mass is approximately 10 times higher after pretreatment with OncoTCS.

Figure 11:
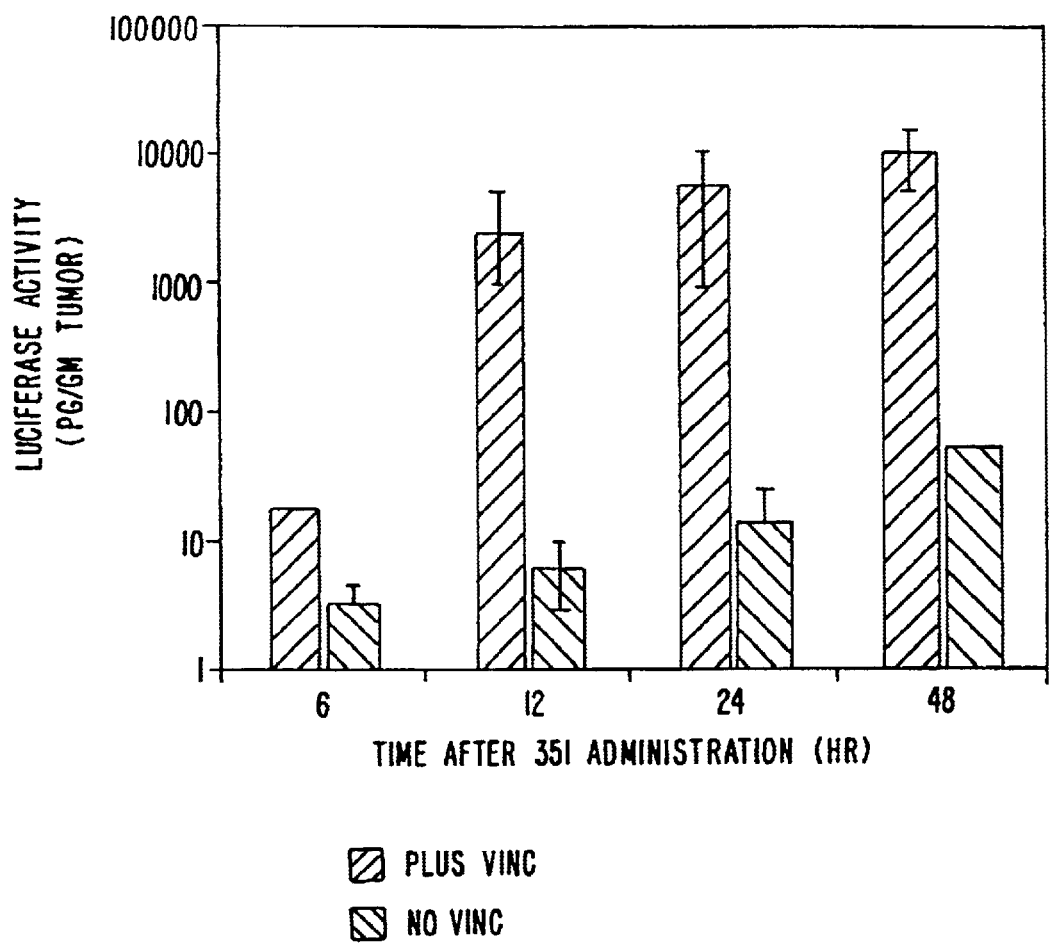
FIG. 11: Effect of OncoTCS pretreatment (i.v., 0.5 mg/kg) on transfection after i.t. administration of INEX 351 (2 µg DNA) into U87 subcutaneous tumors.

The results of FIG. 11 were obtained using U87 tumor bearing mice. U87 tumor cells (ATCC #HTB-14). These cells were prepared and seeded subcutaneously on the hip flank of C57 bl/6 mice according to standard techniques described above. FIG. 11 demonstrates the effect of OncoTCS pretreatment (0.5 mg/kg, i.v.) on transfection and expression of luciferase after i.t. administration of INEX 351 (2 μDNA pINEX L018; approximate lipid dose=10 μg; total volume 20 μL) into U87 tumors. At all time points after administration of DNA (6, 12, 24 and 48 h), an approximate 100-fold improvement in luciferase expression per gram tumor is identified.

b. Systemic Administration of Reporter Gene DNA (pINEX L018) into Spleen Cells (Normal Somatic Tissue) of Tumor Bearing Mice This example demonstrates that pretreatment of mice with Vincristine improves transfection and expression in normal cells (i.e., spleen) of reporter gene construct pINEX L018 encapsulated in an INEX 324 lipid formulation administered by systemic (i.e., intravenous) injection. These results clearly demonstrate that proper selection of the interval between the administration of the cell cycle blocking agent and the administration of the nucleic acid is useful to obtain the greatest improvement in expression levels.

C57 BL/6 mice are seeded subcutaneously with MCA 207 tumor cells. Tumor seeding is performed by standard techniques. Mice were seeded subcutaneously on the hip flank with 100,000 MCA-207 fibrosarcoma tumor cells by intradermal injection on day zero. The tumor cells had been cultivated and prepared according to standard techniques using RPMI media with 10% Fetal Bovine Serum (see, for example, *Current Protocols in Molecular Biology*, Eds. Ausubel, F. M., et al.)

On days 7–10, when tumors had developed to useable sizes, mice were injected i.v. via tail vein with approx. 0.5 mg/kg of OncoTCS (200 μL). Vincristine sulfate in the free form may also be used in known therapeutic dosages. Control mice were injected with empty SM/chol liposomes.

At 8, 16, 24, 30, 36, 42 or 40 hrs after OncoTCS treatment, the mice were injected i.v. via tail vein with INEX 324 (100 μg DNA pINEX-11-12 with about 500 μg lipid all in about 200 μL total volume). Control mice received HBS 8 hr after TCS administration, mice were euthanized and the spleens harvested and analyzed for luciferase activity. Harvested tumors were fast frozen and stored at −70° C. until analyzed for luciferase activity.

Luciferase assay: The frozen tissues are thawed to room temperature. 600–800 μL of 1× cell culture lysis buffer (Promega) is added and the samples are homogenized in the FASTPREP homogenizer for 20 sec at speed 4.0. The samples are centrifuged for 2 min at 10,000 g and 20 μL of the supernatant is assayed for luciferase using standard techniques.

Figure 12:
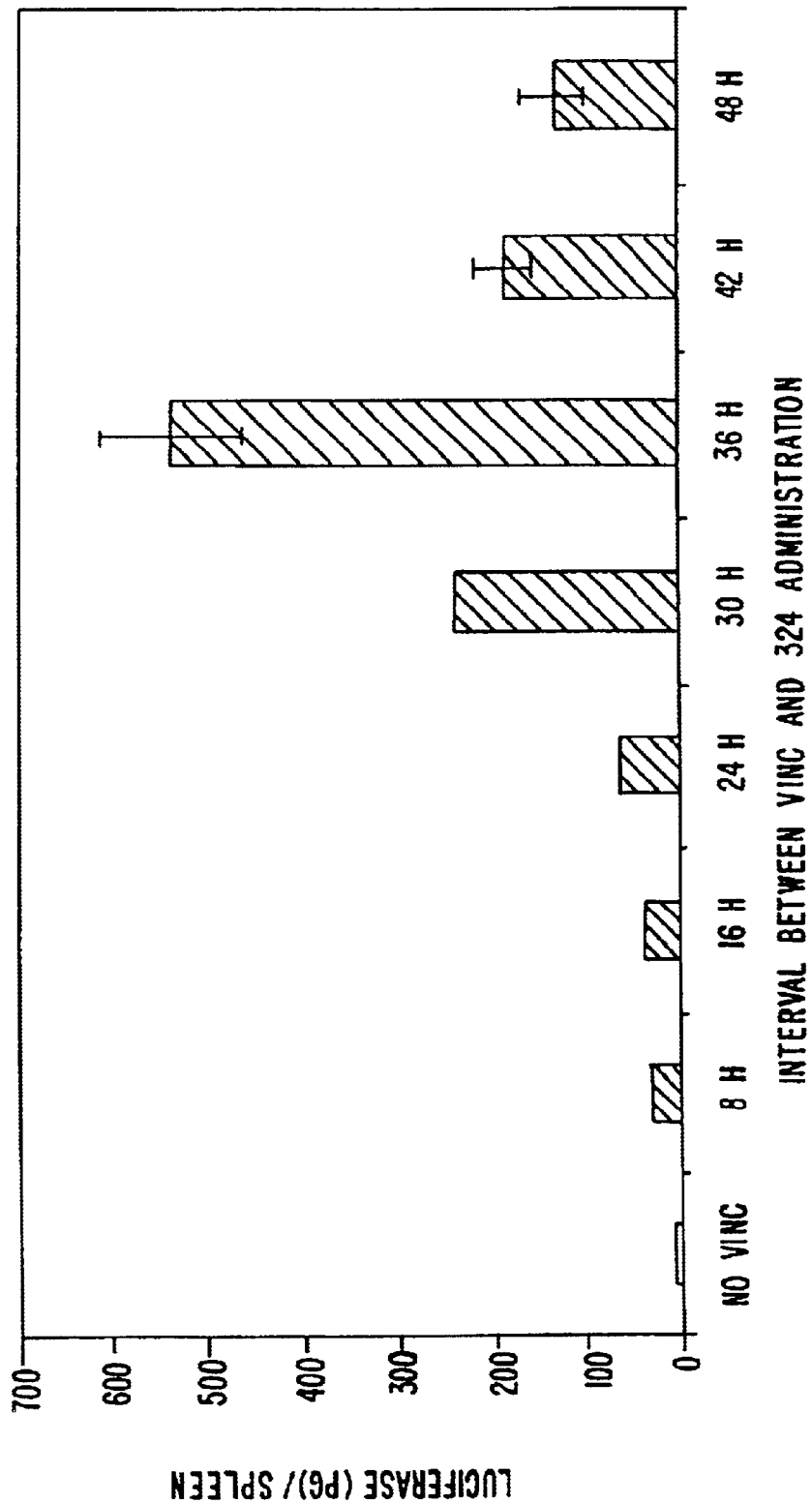
FIG. 12: Effect of length of interval between OncoTCS (i.v. 0.5 mg/kg) treatment and INEX 324 (i.v., 75 µg DNA) administration in spleen cells harvested 8 h after plasmid administration.

FIG. 12 demonstrates an enhanced level (up to 100-fold) of luciferase activity at the spleen after pretreatment with OncoTCS, according to this example. The level of gene expression is dependent on the interval between OncoTCS pretreatment and INEX 324 administration with maximum difference (~100-fold) observed at 36 hr interval. This experiment confirms a principle of the invention that selection of the appropriate interval between administration of the cell cycle blocking agent and administration of a nucleic acid can leading to greatly improved expression of an expressible gene. This experiment also demonstrates that improved transfection and expression of nucleic acids following pretreatment with a cell cycle blocking agent can be obtained at cells other than tumor cells.

c. In vivo Combination Therapy Employing Expressible Nucleic Acids and Conventional Drugs #1

This example demonstrates that pretreatment of mice with vincristine improves therapeutic efficacy of therapeutic gene construct pINEX-IL-12 encapsulated in an INEX 324 lipid formulation administered by systemic (i.e., intravenous) injection.

C57 BL/6 mice are seeded subcutaneously with MCA 207 tumor cells. Tumor seeding is performed by standard techniques. Mice were seeded subcutaneously on the hip flank with 100,000 MCA-207 fibrosarcoma tumor cells by subcutaneous injection on day zero. The tumor cells had been cultivated and prepared according to standard techniques using RPMI media with 10% Fetal Bovine Serum (see, for example, *Current Protocols in Molecular Biology*, Eds. Ausubel, F. M., et al.)

On days 7–10, when tumors had developed to useable sizes, mice were injected i.v. via tail vein with approximately 0.5 mg/kg of OncoTCS (200 μL).

At 8, 16, 24, 30, 36, 42 or 40 hrs after OncoTCS treatment, the mice were injected i.v. via tail vein with INEX 324 (100 μg DNA pINEX-1L-12 with about 500 μg lipid all in about 200 μL total volume). Control mice received HBS. Mice are observed and tumor sizes are recorded daily employing standard measurement techniques using calipers.

Results demonstrate that a subtherapeutic dose of vincristine greatly enhances the therapeutic effect of the pINEX-1L-12 construct in INEX 324 formulation. Tumor growth is inhibited and regression in tumor size is visible.

This experiment demonstrates the use of the invention to treat cancer by causing transfection at sites other than the tumor itself. The mechanism may result from selective transfection of normal somatic cells, such as in the spleen, using genes encoding immune stimulatory agents such as interleukin 12 (IL-12), which cause an effect at a distal site.

d. In vivo Combination Therapy Employing Expressible Nucleic Acids and Conventional Drugs #2

This example demonstrates that the in vivo therapeutic efficacy of an expressible nucleic acid in an SPLP administered by systemic (i.e., intravenous) injection can be improved by pretreatment of the subject with a conventional drug. The conventional drug is a subtherapeutic amount of vincristine; the SPLP is the same HSV-TK/ganciclovir suicide gene system disclosed in U.S. Provisional Patent Application Ser. No, 60/086,917, which is entitled "Systemic Delivery of Serum Stable Plasmid Lipid Particles For Cancer Therapy," and which is assigned to the assignee of the instant invention and is incorporated herein by reference. In the examples disclosed therein, INEX 303 containing the HSV-TK gene plasmid construct demonstrated therapeutic efficacy against tumors when administered intravenously in conjunction with the prodrug ganciclovir. This example demonstrates that the previous work can be improved by pretreatment with a cell cycle blocking agent.

C57 BL/6 mice are seeded subcutaneously with MCA 207 tumor cells. Tumor seeding is performed by standard techniques. Mice are seeded subcutaneously on the hip flank with 100,000 MCA-207 fibrosarcoma tumor cells by intradermal injection on day zero. The tumor cells are cultivated and prepared according to standard techniques using RPMI media with 10% Fetal Bovine Serum (see, for example, *Current Protocols in Molecular Biology*, Eds. Ausubel, F. M., et al.)

On days 7–10, when tumors had developed to useable sizes, mice are injected i.v. via tail vein with approximately 0.5 mg/kg of OncoTCS (200 μL), as described in the other examples.

At 8, 16, 24, 30, 36, 42 or 40 hrs after OncoTCS treatment, the mice are injected i.v. via tail vein with INEX 303 containing pINEX-TK10 prepared as described herein (100 μg DNA with about 500 μg lipid all in about 200 μL total volume). Control mice receive HBS.

1 mg ganciclovir, which is in 200 μL PBS (approximately 50 mg/kg; commercially available from Hoffman La Roche) is administered by intraperitoneal injection 12 h and 24 h after SPLP administration. Mice are observed and tumor sizes are recorded daily employing standard measurement techniques using calipers.

Results demonstrate pretreatment of subjects with a subtherapeutic level of cell cycle blocker inhibits growth of tumors and promotes tumor regression to a significantly greater degree than simply using the HSV-TK/ganciclovir system alone, Additionally, the subtherapeutic dose of vincristine reduces its toxic side effects and makes treatment more tolerable for patients.

e. In vivo Combination Therapy Employing Expressible Nucleic Acids and Conventional Drugs #3

This example demonstrates that the expression of expressible gene construct pINEX L018 encapsulated in an INEX 303 SPLP administered by systemic (i.e., intravenous) injection can be substantially increased by choosing the proper period interval between administration of the SPLP and the cell cycle blocking agent. It is found that a shift of as little as 8 hours can increase expression, in vivo, by three-fold or more.

A/J mice (Harlan Sprague Dawley or Charles River Laboratory) are seeded subcutaneously with Neuro2a tumor cells (neurological tumor #CLL 131). Tumor cells were prepared and seeded using standard techniques. Mice were seeded on the hip flank with 1.5 million tumor cells by subcutaneous injection on day zero. The tumor cells had been cultivated and prepared according to standard techniques using RPMI media with 10% Fetal Bovine Serum (see, for example, *Current Protocols in Molecular Biolog*, Eds. Ausubel, F. M., et al.). Experiments were performed starting on days 7–10, when tumors had developed to useable sizes (30–100 mg).

In these experiments, the tumored mice were injected i.v. via tail vein with INEX 303 (100 μg DNA pINEX L018 with about 500 μg lipid all in about 200 μL total volume). Control mice received HBS (buffer only). In each case, mice were euthanized and sacrificed 48 hours after plasmid administration. Tumors were immediately removed from the mice and flash frozen and stored until luciferase expression activity in the tumor could be measured according to standard techniques.

Figure 14:
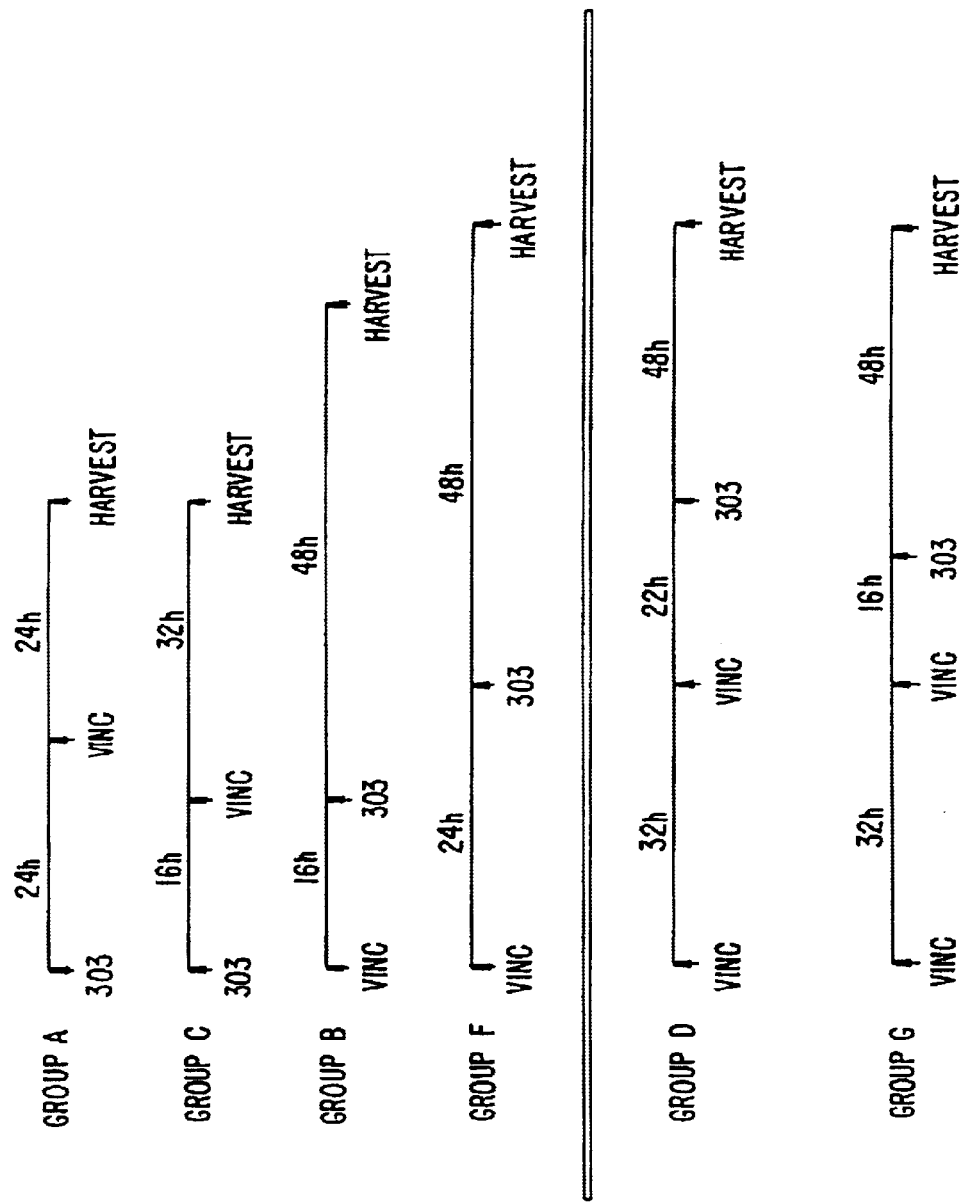
FIG. 14 sets forth the schedule of vincristine administrations.

FIG. 14 sets out the schedule of vincristine administrations. In each case, mice were injected i.v. via tail vein with approximately 0.5 mg/kg of OncoTCS (200 μLs). The schedule sets out the OncoTCS (i.e., vine) administration schedule. OncoTCS was administered either before or after the plasmid, and two doses of OncoTCS were sometimes administered.

The relative timing of administrations reflects the strategy of optimizing the delivery of the Inex 303 to the tumor site, and coordinating that delivery with the release of cells from the cell cycle blacker. Inex 303 is a relatively long circulating formulation, so accumulation of large doses at the tumor site requires longer time periods.

Figure 15:
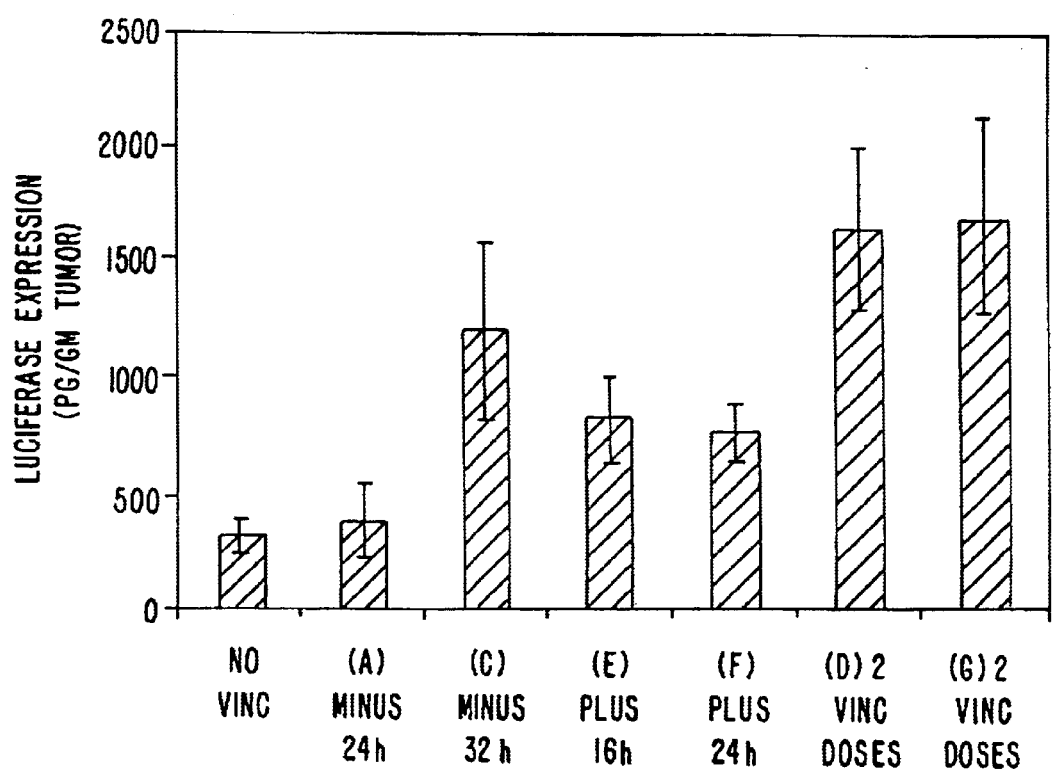
FIG. 15 illustrates the effect of vincristine on transfection using INEX 303 on neuro 2 a tumors.

Results in FIG. 15 demonstrate an exquisite sensitivity of the tumors to the relative timing of OncoTCS and SPLP administrations. Groups A and C demonstrate that when SPLP is administered in advance of OncoTCS, expression is about three times greater if the tumors are exposed to vincristine for an extra 8 hours (i.e., 32 h instead of 24 h). Groups E and F demonstrate that this 8 hour effect is not significant when the OncoTCS is administered 64–72 h before tumor harvest. It is suggested from this data that a critical parameter for improved gene expression, when the timing of SPLP administration to tumor harvest is fixed at 48 hours, is the total amount of time from OncoTCS administration to harvest. The relative scheduling of OncoTCS administration for improved gene expression is 32 h>64 h=72 h>24 h.

FIG. 15 also shows that two doses of OncoTCS in advance of SPLP administration result in an approximately 4-fold increase in luciferase expression at the tumor compared to controls (Groups D and G vs. Group E). It is drought that the great improvement in luciferase expression may be attributed to the extra dose of OncoTCS, which is approaching therapeutic levels.

Figure 16:
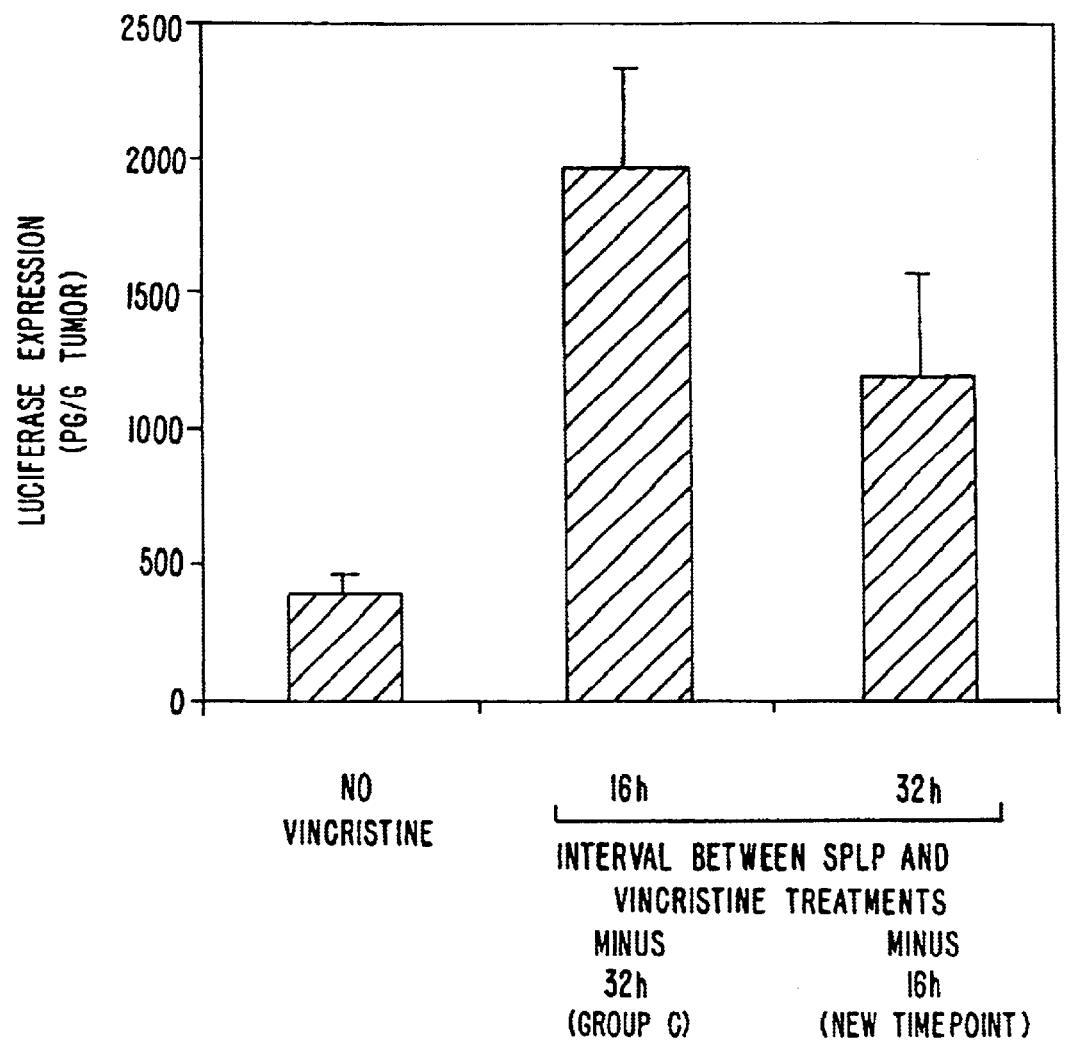
FIG. 16 illustrates luciferase expression at the in vivo tumor site 48 h after INEX 303 administration and 0, 32 h and 16 h after OncoTCS administration.

FIG. 16 demonstrates, in a repeat experiment, that Group C (minus 32 h) shows greater transfection than a minus 16 h time point.

11. In vivo Combination Therapy Employing Expressible Nucleic Acids and X-rays

This example demonstrates that improved expression of nucleic acids can also be achieved using an alternative method of synchronizing cells, namely, X-ray therapy. Again, proper selection of the interval between the administration of the cell cycle blocking agent and the administration of the nucleic acid is useful to obtain greatest improvement in expression levels.

C57 BL/6 mice are seeded intraperitoneally with B16 tumor cells (CRL 6322). Tumor seeding was performed by standard techniques. Mice were seeded intraperitoneally with 100,000 B16 tumor cells by injection on day zero. The tumor cells had been cultivated and prepared according to standard techniques using RPMI media with 10% Fetal Bovine Serum (see, for example, *Current Protocols Molecular Biology*, Eds. Ausubel, F. M., et al.)

After 8 days, mice were irradiated 4 times (whole mouse; 6 Gy, 250 keV) 8–12 hours apart. Control mice were not irradiated (n=5 for each group). At 36 hrs after the last radiation dose, all mice were injected intraperitoneally with 25 μg of SPLP INEX 324 containing pINEX L018 (5 μg DNA with about 20 μg lipid all in about 200 μL total volume). Control mice received HBS. 24 hr after SPLP administration, mice were euthanized and the tumors harvested and analyzed for luciferase activity. Harvested tumors were fast frozen and stored at −70° C. until analyzed for luciferase activity.

Luciferase assay: The frozen tissues are thawed to room temperature. 600–800 μL1 of 1× cell culture lysis buffer (Promega) is added, and the samples are homogenized in the FASTPREP homogenizer for 20 sec at speed 4.0. The samples are centrifuged for 2 min at 10,000 g and 20 μL of the supernatant is assayed for luciferase using standard techniques.

Figure 13:
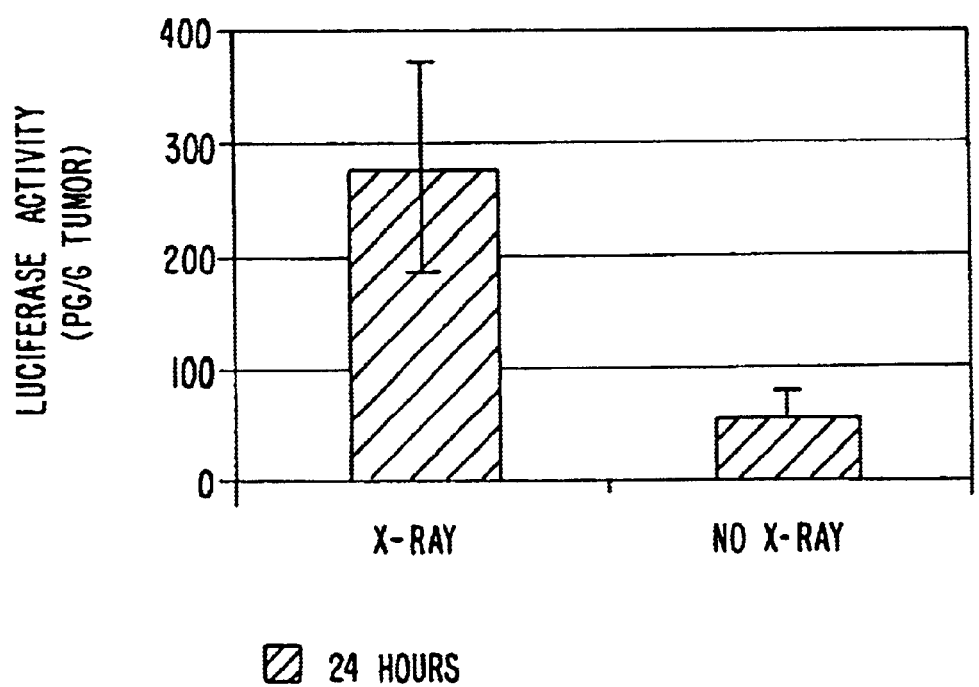
FIG. 13: Effect of X-rays on luciferase activity in i.p. B16 tumors after i.p. administration of INEX 324.

FIG. 13 demonstrates the effect of X-rays on luciferase activity in i.p. B16 tumors after i.p. administration of SPLP INEX 324 containing pINEX L018. An approximately 5-fold enhanced level of luciferase activity is detected in i.p. tumors after pretreatment with X-Rays, compared with nonpretreated animals. This result confirms the principle of using pretreatment with X-rays to synchronize tumor cells at a certain stage of the cell cycle, following which expression of transduced nucleic acids are improved.

It is understood that the examples and embodiments described herein are for illustrative purposes only and that various modifications or changes in light thereof will be suggested to persons skilled in the art and are to be included within the spirit and purview of this application and scope of the appended claims. All publications, patents and patent applications cited herein are hereby incorporated by reference for all purposes.

What is claimed is:

1. A method of introducing a nucleic acid encoding a foreign gene into a cell in a patient, said method comprising the steps of
   (a) fast administering a cell cycle blocking agent to said patient, wherein said cell cycle blocking agent is a member selected front the group consisting of cyclophosphamide, taxol, taxolene, and a vinca alkaloid; and
   (b) second administering said nucleic acid to said patient within seven days of step (a), wherein transfection efficiency is increased by at least 50%.

2. The method of claim 1 wherein step (b) is performed within 3 days of step (a).

3. The method of claim 1 wherein step (b) is performed within 24 hours of step (a).

4. The method of claim 1 wherein said foreign gene is a plasmid.

5. The method of claim 1 wherein said foreign gene comprises a gene selected from the group consisting of genes encoding a cytokine, apoptotic protein, tumor suppressor, heat shock protein, immunogenic antigen, pro-

SEQUENCE LISTING

```
<160> NUMBER OF SEQ ID NOS: 2

<210> SEQ ID NO 1
<211> LENGTH: 15
<212> TYPE: PRT
<213> ORGANISM: Artificial Sequence
<220> FEATURE:
<221> NAME/KEY: MOD_RES
<222> LOCATION: (2)
<223> OTHER INFORMATION: Xaa = Ile or Leu
<220> FEATURE:
<221> NAME/KEY: MOD_RES
<222> LOCATION: (3)
<223> OTHER INFORMATION: Xaa = Phe or Leu
<220> FEATURE:
<221> NAME/KEY: MOD_RES
<222> LOCATION: (10)
<223> OTHER INFORMATION: Xaa = Ala or Val
<220> FEATURE:
<221> NAME/KEY: MOD_RES
<222> LOCATION: (11)
<223> OTHER INFORMATION: Xaa = Val or Met
<220> FEATURE:
<223> OTHER INFORMATION: Description of Artificial Sequence:herpes
      simplex virus thymidine kinase gene (HSV-TK) peptide encoded by
      pINEX TK10 plasmid construct

<400> SEQUENCE: 1

Leu Xaa Xaa Asp Arg His Pro Ile Ala Xaa Xaa Leu Cys Tyr Pro
1               5                   10                  15

<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence:fusogenic
      peptide

<400> SEQUENCE: 2

Glu Ala Leu Ala
1
``` teinase inhibitor, anti-angiogenic protein, suicide gene for use in GDEPT, ribozyme, antisense nucleic acid, viral protein and a toxin.

6. The method of claim 1 wherein said foreign gene is administered systemically.

7. The method of claim 1 wherein said foreign gene is administered locally or regionally.

8. The method of claim 1, wherein said cell cycle blocking agent is a member selected from the group consisting of cyclophosphamide, taxol, and vincristine.

9. The method of claim 1 wherein said cell cycle blocking agent is in a lipsome formulation.

10. A method of claim 1 wherein said cell cycle blocking agent is administered at least 32 h prior to administering said foreign gene.

11. A method of claim 1 wherein said cell cycle blocking agent is administered at least 48 h prior to administering said foreign gene.

12. The method of claim 1, wherein the vinca alkaloid is a member selected from the group consisting of vinblastine, vincristine, and vinorelbine.

13. The method of claim 1, wherein said lipid formulation is prepared by the method comprising:
   (a) contacting said nucleic acid with a solution comprising non-cationic lipids and a detergent to form a nucleic acid-lipid mixture;
   (b) contacting cationic lipids with the nucleic acid-lipid mixture, thereby forming a charge-neutralized mixture of nucleic acids and lipids; and
   (c) removing the detergent from the charge-neutralized mixture to provide the lipid-nucleic acid particles in which the nucleic acids are protected from degradation.

14. The method of claim 1, wherein the foreign gene is a therapeutic gene.

15. A method of inhibiting growth of cancer cells in a patient having a cancer comprising introducing a nucleic acid encoding a foreign gene into a cell in a patient having cancer, said method comprising the steps of:
   (a) first administering a cell cycle blocking agent to said patient, wherein said cell cycle blocking agent is a member selected from the group consisting of cyclophosphamide, taxol, taxolene, and a vinca alkaloid; and
   (b) second administering said nucleic acid to said patient within seven days of step (a), wherein said nucleic acid is administered systemically, and wherein transfection efficiency is increased by at least 50%.

16. The method of claim 15, wherein said cancer comprises a tumor.

17. The method of claim 16, wherein said cell cycle blocking agent and said foreign gene are administered distal to the site of the tumor.

18. The method of claim 15, wherein said cell cycle blocking agent or said foreign gene are administered intravenously.

19. The method of claim 15, wherein said cell cycle blocking agent or said foreign gene is administered intraperitoneally.

20. The method of claim 15, wherein the vinca alkaloid is a member selected from the group consisting of vinblastine, vincristine, and vinorelbine.

21. The method of claim 15, wherein the foreign gene is a therapeutic gene.

22. A method of treating a patient having a cancer comprising introducing a nucleic acid encoding a foreign gene into a call in said patient, said method comprising the steps of:
   (a) first administering a cell cycle blocking agent to said patient, wherein said cell cycle blocking agent is a member selected from the group consisting of cyclophosphamide, taxol, taxolene, and a vinca alkaloid; and
   (b) second administering said nucleic acid to said patient within seven days of step (a), wherein said nucleic acid is administered in a lipid formulation comprising a cationic lipid and a lipid derivative selected from the group consisting of an ATTA-lipid, a polyethylene glycol (PEG)-lipid derivative, and a ganglioside $G_{M1}$-modified lipid,
   wherein said nucleic acid is fully encapsulated in said lipid formulation such that less than 5% of the nucleic acid is degraded after exposure of said formulation to 1 U DNAse I for 30 minutes in digestion buffer at 37° C., and
   further wherein transfection efficiency is increased by at least 50%.

23. The method of claim 22, wherein said (PEG)-lipid derivative is a PEG-ceramide.

24. The method of claim 23, wherein said PEG-ceramide is a member selected from the group of PEG-Cer-C14, PEG-Cer-C20, and PEG-Cer-C8.

25. The method of claim 22, wherein said lipid derivative is present in an amount of from about 1% to about 20% by weight of the lipid formulation.

26. The method of claim 22, wherein said lipid formulation is prepared by the method comprising:
   (a) contacting said nucleic acid with a solution comprising non-cationic lipids and a detergent to form a nucleic acid-lipid mixture;
   (b) contacting said cationic lipid with the nucleic acid-lipid mixture, thereby forming a charge-neutralized mixture of nucleic acids and lipids; and
   (c) removing the detergent from the charge-neutralized mixture to provide the lipid-nucleic acid particles in which the nucleic acids are protected from degradation.

27. The method of claim 22, wherein the vinca alkaloid is a member selected from the group consisting of vinblastine, vincristine, and vinorelbine.

28. The method of claim 22, wherein the foreign gene is a therapeutic gene.

29. The method of claim 1 wherein said cell cycle blocking agent is selected from the group consisting of DNA alkylating agents, DNA topoisomerase inhibitors, microtuble disassmebly inhibitors, microtubule disassembly inhibitors, DNA-cross linking agents, DNA-binding agents and nuceleoside analogues.

* * * * *

UNITED STATES PATENT AND TRADEMARK OFFICE
CERTIFICATE OF CORRECTION

PATENT NO. : 6,841,537 B1
DATED : January 11, 2005
INVENTOR(S) : Joshi et al.

It is certified that error appears in the above-identified patent and that said Letters Patent is hereby corrected as shown below:

Column 36,
Line 13, please replace "leading" with -- lead --.

Column 40,
Line 5, please replace "fast" with -- first --.
Line 7, please replace "front" with -- from --.
Line 11, after "step (a)," please insert -- wherein said nucleic acid is administered in a lipid formulation comprising a cationic lipid and a lipid derivative selected from the group consisting of an ATTA-lipid, a polyethylene glycol (PEG)-lipid derivative, and a ganglioside $G_{M1}$-modified lipid,
 wherein said nucleic acid is fully encapsulated in said lipid formulation such that less than 5% of the nucleic acid is degraded after exposure of said formulation to 1 U DNAse I for 30 minutes in digestion buffer at 37°C, and
further --.

Column 41,
Line 2, please replace "GDEPT" with -- Gene Directed Enzyme Prodrug Therapy ("GDEPT") --.
Column 41, Line 47, please replace ", and" with --in a lipid formulation comprising a cationic lipid and a lipid derivative selected from the group consisting of an ATTA-lipid, a polyethylene glycol (PEG)-lipid derivative, and a ganglioside $G_{M1}$-modified lipid,
 wherein said nucleic acid is fully encapsulated in said lipid formulation such that less than 5% of the nucleic acid is degraded after exposure of said formulation to 1 U DNAse I for 30 minutes in digestion buffer at 37°C, and
further, --.

UNITED STATES PATENT AND TRADEMARK OFFICE
CERTIFICATE OF CORRECTION

PATENT NO. : 6,841,537 B1
DATED : January 11, 2005
INVENTOR(S) : Joshi et al.

It is certified that error appears in the above-identified patent and that said Letters Patent is hereby corrected as shown below:

Column 42,
Line 8, please replace "call" with -- cell --.
Lines 52 to 57, please delete "29. The method of claim 1, wherein said cell cycle blocking agent is selected from the group consisting of DNA alkylating agents, DNA topoisomerase inhibitors, micro-tuble disassembly inhibitors, microtubule disassembly inhibitors, DNA-cross linking agents, DNA-binding agents and nuceleoside analogues."

Signed and Sealed this

Thirty-first Day of May, 2005

JON W. DUDAS
*Director of the United States Patent and Trademark Office*